(12) United States Patent
Mills, Jr. et al.

(10) Patent No.: US 6,696,285 B1
(45) Date of Patent: Feb. 24, 2004

(54) NANOMACHINES FUELED BY NUCLEIC ACID STRAND EXCHANGE

(75) Inventors: Allen P. Mills, Jr., Chatham, NJ (US); Bernard Yurke, Plainfield, NJ (US)

(73) Assignee: Lucent Technolgies Inc., Murray Hill, NJ (US)

( * ) Notice: Subject to any disclaimer, the term of this patent is extended or adjusted under 35 U.S.C. 154(b) by 0 days.

(21) Appl. No.: 09/496,346

(22) Filed: Feb. 2, 2000

Related U.S. Application Data

(63) Continuation-in-part of application No. 09/167,971, filed on Oct. 8, 1998, now abandoned, which is a continuation-in-part of application No. 09/139,105, filed on Aug. 25, 1998, now abandoned.

(51) Int. Cl.[7] .............................. C12M 1/00; C12Q 1/68; G01N 1/00; B01J 8/00
(52) U.S. Cl. ..................... 435/285.1; 435/6; 435/286.1; 435/289.1; 422/50; 422/129
(58) Field of Search ....................... 422/50, 129; 435/6, 435/285.1, 286.1, 289.1; 536/23.1

(56) References Cited

PUBLICATIONS

Ellwood et al., Clinical Chemistry, vol. 32, No. 9, pp. 1631–1636, 1986.*

Matthews et al., Analytical Biochemistry, vol. 169, pp. 1–25, 1988.*

* cited by examiner

*Primary Examiner*—Ardin H. Marschel

(57) ABSTRACT

The rate of nucleic acid strand exchange can be greatly enhanced if one of the strands of a double-stranded nucleic acid oligomer has a single-stranded extension, or "toehold," to which a complementary, single-stranded, nucleic acid oligomer can bind. Toehold-facilitated strand exchange makes possible the controlled addition and removal of one nucleic acid strand from a second, complementary strand. Oligomers are designed and used to carry out controlled, repetitive nucleic acid structural transitions mediated by hybridization and toehold-facilitated strand exchange reactions, which in turn control the operation of a nanomachine or a 2-state molecular switch.

23 Claims, 14 Drawing Sheets

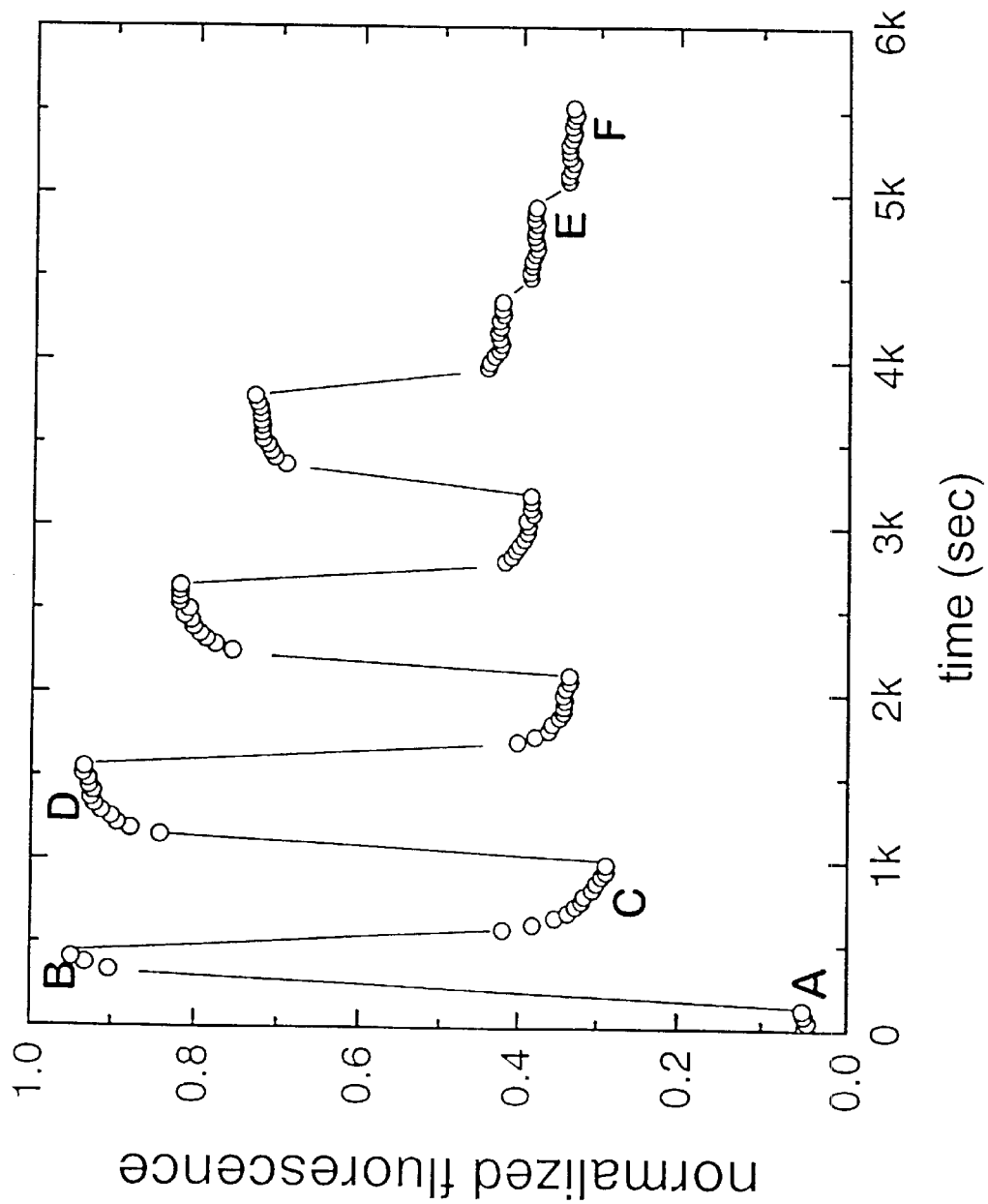

SEQUENCE LISTING

<160> NUMBER OF SEQ ID NOS: 13

<210> SEQ ID NO 1
<211> LENGTH: 33
<212> TYPE: DNA
<213> ORGANISM: Artificial Sequence
<220> FEATURE:
<223> OTHER INFORMATION: Description of Artificial Sequence:
      Oligonucleotide which is part of or controls a nanodevice

<400> SEQUENCE: 1
agtacggaca ctagctggat ctgaggatta gta                              33

<210> SEQ ID NO 2
<211> LENGTH: 27
<212> TYPE: DNA
<213> ORGANISM: Artificial Sequence
<220> FEATURE:
<223> OTHER INFORMATION: Description of Artificial Sequence:
      Oligonucleotide which is part of or controls a nanodevice

<400> SEQUENCE: 2
aactaatcct cagatccagc tagtgtc                                    27

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence:
      Oligonucleotide which is part of or controls a nanodevice

<400> SEQUENCE: 3
actaatcctc agatccagct                                            20

<210> SEQ ID NO 4
<211> LENGTH: 22
<212> TYPE: DNA
<213> ORGANISM: Artificial Sequence
<220> FEATURE:

```
<223> OTHER INFORMATION: Description of Artificial Sequence:
      Oligonucleotide which is part of or controls a nanodevice

<400> SEQUENCE: 4
actaatcctc agatccagct ag                                              22

<210> SEQ ID NO 5
<211> LENGTH: 24
<212> TYPE: DNA
<213> ORGANISM: Artificial Sequence
<220> FEATURE:
<223> OTHER INFORMATION: Description of Artificial Sequence:
      Oligonucleotide which is part of or controls a nanodevice

<400> SEQUENCE: 5
actaatcctc agatccagct agtg                                            24

<210> SEQ ID NO 6
<211> LENGTH: 26
<212> TYPE: DNA
<213> ORGANISM: Artificial Sequence
<220> FEATURE:
<223> OTHER INFORMATION: Description of Artificial Sequence:
      Oligonucleotide which is part of or controls a nanodevice

<400> SEQUENCE: 6
actaatcctc agatccagct agtgtc                                          26

<210> SEQ ID NO 7
<211> LENGTH: 28
<212> TYPE: DNA
<213> ORGANISM: Artificial Sequence
<220> FEATURE:
<223> OTHER INFORMATION: Description of Artificial Sequence:
      Oligonucleotide which is part of or controls a nanodevice

<400> SEQUENCE: 7
actaatcctc agatccagct agtgtccg                                        28

<210> SEQ ID NO 8
<211> LENGTH: 30
<212> TYPE: DNA
<213> ORGANISM: Artificial Sequence
<220> FEATURE:
<223> OTHER INFORMATION: Description of Artificial Sequence:
      Oligonucleotide which is part of or controls a nanodevice

<400> SEQUENCE: 8
actaatcctc agatccagct agtgtccgta                                      30

<210> SEQ ID NO 9
<211> LENGTH: 32
<212> TYPE: DNA
<213> ORGANISM: Artificial Sequence
<220> FEATURE:
<223> OTHER INFORMATION: Description of Artificial Sequence:
      Oligonucleotide which is part of or controls a nanodevice

<400> SEQUENCE: 9
actaatcctc agatccagct agtgtccgta ct                                   32

<210> SEQ ID NO 10
<211> LENGTH: 40
<212> TYPE: DNA
<213> ORGANISM: Artificial Sequence
<220> FEATURE:
```

-continued

```
<223> OTHER INFORMATION: Description of Artificial Sequence: Synthetic
      oligonucleotide

<400> SEQUENCE: 10
tgccttgtaa gagcgaccat caacctggaa tgcttcggat                           40

<210> SEQ ID NO 11
<211> LENGTH: 44
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
atggtcgctc ttacaaggca ctggtaacaa tcacggtcta tgcg                     44

<210> SEQ ID NO 12
<211> LENGTH: 44
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
ggagtcctac tgtctgaact aacgatccga agcattccag gttg                     44

<210> SEQ ID NO 13
<211> LENGTH: 56
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
cgcatagacc gtgattgtta ccagcgttag ttcagacagt aggactcctg ctacga        56
```

NANOMACHINES FUELED BY NUCLEIC ACID STRAND EXCHANGE

CROSS-REFERENCES TO RELATED APPLICATIONS

This application is a continuation-in-part of U.S. application Ser. No. 09/167,971 filed Oct. 8, 1998, now abandoned, which is a continuation-in-part of U.S. application Ser. No. 09/139,105 filed Aug. 25, 1998; abandoned.

FIELD OF THE INVENTION

The free energy of hybridization of complementary hybridizing oligomers such as nucleic acids and nucleic acid analogs can be directed to effect controlled and reversible changes in the configuration of molecular structures, and so can be used to control a molecular switch, or can serve as fuel to drive the motion of a nanomachine. This invention pertains to methods in which oligomer hybridization/displacement reactions operate a reversible molecular switch, or fuel a nanomachine. The methods of the invention comprise controlling the number and type of hybridizing subunits, e.g., nucleotides, in single-stranded "toehold" regions that extend from double-stranded oligomer complexes attached to the molecular switches or nanomachines. The single-stranded toehold regions enhance the rate with which single-stranded oligomers hybridize to and displace one of the strands of such double-stranded complexes to reversibly alter the configuration of the molecular switches or nanomachines. The invention further includes molecular switches and nanomachines comprising molecular structures which reversibly assume alternate configurations at molecular reaction rates that are controlled by hybridization reactions involving said oligomers comprising single-stranded "toehold" regions.

BACKGROUND OF THE INVENTION

Toehold-Mediated Strand Displacement

It has been shown that a single-stranded region of a nucleic acid extending from the end of a double-stranded (duplex) complex formed by hybridization of two strands of unequal length provides a nucleation site, or "toehold," for hybridization of a third nucleic acid strand complementary to the longer strand. A toehold-mediated hybridization/displacement reaction is initiated when a portion of the third strand hybridizes to the single-stranded toehold sequence, and proceeds with the remaining portion of the third strand subsequently hybridizing to the longer strand while displacing the shorter strand. The rate of strand displacement by such a toehold-mediated hybridization/displacement reaction is considerably greater than the rate of the strand displacement reaction when there is no toehold region [1–3]. Methods utilizing toehold-mediated hybridization/displacement reactions have been developed for detecting nucleic acids having specific nucleotide sequences [2, 3], and for ligating linker oligonucleotides to nucleic acids having specific nucleotide sequences to facilitate detection, affinity chromatography, and cloning of the nucleic acids [4, 5].

There have been several studies of the effects of varying biochemical and physical parameters of the toehold-mediated hybridization/displacement on the rate of the reaction. The overall rate of a toehold-mediated strand-displacement reaction is limited by the rate of association of the "incoming" displacing strand with the toehold region; the displacement of the shorter strand is not rate-limiting ([2], p. 1635; and [6], p. 4210). Once the displacing strand associates with the toehold region and begins displacing the shorter strand, the shorter strand is displaced via double-strand branch migration with a rate of approximately 12 $\mu$sec per nucleotide (determined in 0.3M NaCl, at 65° C.; see [2], p. 1635, and [7], p. 1911). The overall rate of hybridization/displacement reaction is increased by (1) increasing the is temperature, (2) increasing the concentration of the displacing DNA strand, and (3) adding volume-excluding polymers, presumably by increasing the rate of association of the incoming strand with the toehold region ([2], p. 1635; and [8], p. 20). The hybridization/displacement reaction rate is also increased by (4) modifying the displacing DNA strands so that they contain 5-bromodeoxycytidine (BrdC) or 5-methyl-deoxycytidine (MedC) nucleotides, which increase the affinity with which the displacing strand hybridizes to its complementary DNA strand in the duplex ([5], p. 2251; and [6], p. 4207). The rate of the hybridization/displacement reaction can also be increased by (5) increasing the G+C content of the toehold region ([6], p. 4207), (6) adding Rec A protein to the reaction mixture ([8], p. 25), and (7) using a displacing strand which is double-stranded at its terminal portion adjacent to the single-stranded region that binds the toehold sequence ([6], p. 4210). The effects of the lengths of the displacing strand and the displaced strand on the overall reaction rate are not well understood, and appear to be dependent on the nucleotide sequence of the toehold region, and possibly on the nucleotide sequence of the duplex region adjacent to the toehold region (compare [2], p. 1635, and [6], p. 4211). The effects of mismatches between the bases of the incoming, displacing strand and those of the longer, toehold-linked strand on the rate of the strand displacement are also unclear, and appear to depend strongly on the temperature of the reaction. For example, one study reports that a single mismatch blocks branch migration at 55° C. ([4], p. 8680), whereas another study reports that a cluster of 5 mismatches among 7 bases does not reduce the efficiency of strand displacement at 65° C. ([8], pp. 23–24). Interestingly, the latter study also reports that 27% base mismatch over 85 nucleotides blocks strand displacement at 65° C., but not at 55° C. ([8], pp. 23–24). The latter result indicates that displacing strands can be synthesized having a selected number of mismatches so that displacement does not occur unless the temperature is at or above a selected value.

It has been shown that a toehold-mediated hybridization/displacement proceeds approximately 3 times more rapidly with the 4-nucleotide toehold sequence GGCC- than it does with the 3-nucleotide toehold CCG-([6], p. 4211); however, the precise relationship between the length of the toehold region and the rate of the toehold-mediated hybridization/displacement reaction has not been described prior to the present invention.

Molecular Nanotechnology

Molecular nanotechnology uses molecular engineering and manufacturing capabilities, employing the capabilities of biotechnology in combination with other technologies such as proximate probe technology and supramolecular chemistry, to develop nanometer-scale machines and devices assembled from natural and nonnatural macromolecules and other chemical structures [9]. An example of such a molecular device is a controllable two-state molecular switch, which can be used to store information in the same manner as the counters of an abacus, or the electronically operated switches of a computer ([9], pp. 2012–2014).

DNA nanotechnology takes advantage of the self-organizing properties of DNA polymers, and uses DNA oligomers having selected nucleotide sequences as structural elements in the assembly of complex structures on a molecular scale [10–14]. The advantages of using DNA to construct nanodevices include (1) double-stranded DNA molecules of 1–3 turns are relatively rigid structural elements, and the intermolecular interactions of DNA are relatively well-understood and predictable, so that DNA polymers can be designed which will self-assemble in a predictable manner;
(2) oligomers of DNA and its analogs having arbitrary subunit sequences can be produced readily using solid support synthesis;
(3) many different methods for chemically modifying DNA have been developed, e.g. to attach linking functions, catalytic or structural polypeptides, or detectable groups such as biotin and fluorescent labels, and to modify properties of the DNA such as resistance to cleavage by nucleases, hydrophobicity, flexibility, and duplex stability;
(4) DNA can be manipulated by an array of enzymes that include DNA restriction endonucleases, DNA ligase, kinases, and exonucleases; and
(5) the external surface of DNA polymers is rich in structural information, and segments of single- and double-stranded DNA can be recognized and bound by other nucleic acids and by DNA-binding sites of proteins, in DNA-binding reactions having a wide range of specificities and affinities ([10], p. 228).

It has been proposed that DNA structural transitions such as migration of a cruciform branch structure, or the B-Z transition, might be used to drive a nanomechanical device ([10], p. 245). Prior to the present invention, there was no suggestion to capture and use the free energy of the transition from single-stranded DNA to double-stranded DNA to alter the configuration of a molecular switch, or to fuel a molecular machine.

BRIEF SUMMARY OF THE INVENTION

A single-stranded terminal portion of a first nucleic acid strand that extends from an end of a duplex complex formed by hybridization of the first strand to a second, shorter, complementary nucleic acid strand, provides a "toehold" nucleation site for hybridization for a third single-stranded nucleic acid that is also complementary to the first one, and greatly enhances the rate of the hybridization/displacement reaction in which the third nucleic acid displaces the second strand and forms a double-stranded complex with the first strand, relative to the rate when there is no toehold. The present invention pertains to methods in which this toehold-mediated process of enhancing the rate of strand displacement is employed to direct the free energy of nucleic acid hybridization to do useful work; for example, to effect changes in nucleic acid configurations, to produce molecular switches, to fuel molecular machines, to drive molecular reactions, and to produce catalytic, or cascading, reactions which respond to, and permit detection of, very small amounts of a particular nucleic acid. The methods of the present invention employ toehold-mediated strand-displacement to cyclically or reversibly alter the configuration of a molecular nanomachine comprising or attached to one or more "motor" nucleic acid strands. A nanomachine operated by the reversible or cyclical binding of a fuel strand to and from a motor strand according the present invention can function as a molecular motor that periodically applies a discrete, significant force to a portion of a separate molecular device to which it is attached or with which it makes contact. Alternatively, such a nanomachine can operate as a reversibly controllable switch or signalling device; for example, binding of the fuel strand to the motor strand can put the switch in the "on" position, and toehold-mediated displacement of the fuel strand by the removal strand can provide a means for returning the switch to the "off" position. One or more fluorophores can be attached to the nanomachine, to one or more motor strands connected thereto, or to the fuel strands, in such a manner that the change in physical configuration of the nanomachine and motor strands resulting from hybridization of a fuel strand to one or more motor strands results in a change in the fluorescence of a fluorophore, thereby providing a detectable signal indicative of the current configuration of the nanomachine.

Reaction kinetics measurements for the toehold-mediated process of enhancing the rate of nucleic acid strand displacement are disclosed herein which indicate the rates with which such molecular motors, switches, and reactions, could be driven.

BRIEF DESCRIPTION OF THE DRAWINGS

FIG. 1(c) shows conversion of the pump from the relaxed configuration shown in 1(a) to the rigid form shown in 1(b) by hybridization of fuel strand F to strands A and B. The fuel strand is removed through hybridization with the removal strand R as shown in FIG. 1(d). This allows the pump to return to its relaxed configuration 1(a). Fuel strand removal is facilitated by hybridization of the $\overline{C}$ and C regions of the fuel and removal strands. The $\overline{C}$ region of the fuel strand is referred to as a toehold.

FIG. 2: Reaction kinetics data. Fluorescence from the sample vials is plotted as a function of time.

FIG. 4: The fluorescence signal for Q cycled between being unbound or bound to strand S. At A, pure Q is present in buffer solution. When a stoichiometric amount of S is added, Q becomes bound and the fluorescence rises as seen at B. When a stoichiometric amount of $T_6$ is added, Q becomes unbound and the fluorescence drops as seen at C. Q is bound and unbound several more times beyond B through successively adding stoichiometric amounts of S and $T_6$. At E and F extra S is added, doubling and quadrupling the concentration of free S above stoichiometry. The successively degraded recovery after each cycle is attributed to dilution effects and the accumulation of impurities.

DETAILED DESCRIPTION OF THE INVENTION

Figure 1A:
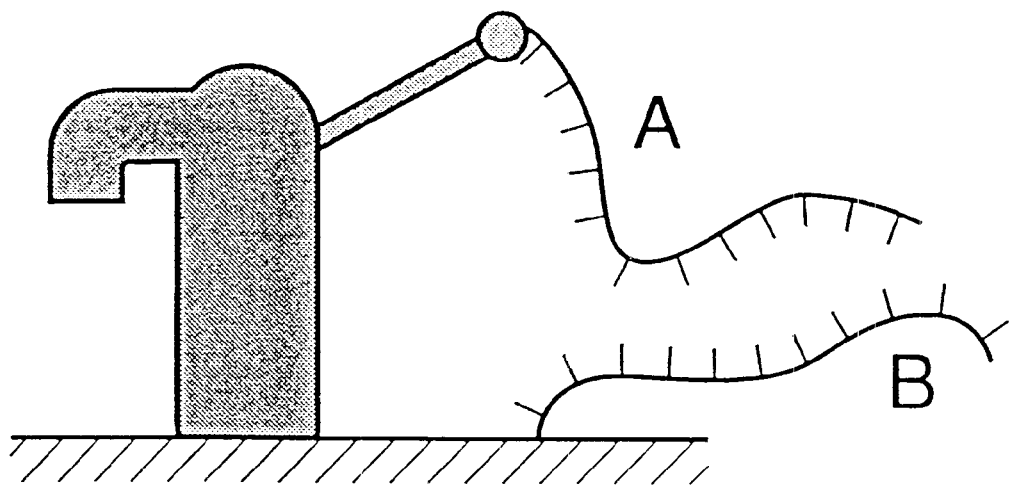
FIGS. 1(a)–1(d): Schematic representations of strands of DNA operating a molecular machine, represented here as a fluid pump. In 1(a) the pump is shown in relaxed position with DNA strand A attached to the pump handle and DNA strand B attached to the substrate, or "floor". In 1(b) the pump is shown at the end of the power stroke performed by fuel strand F as it hybridizes with strands A and B.

Unless otherwise indicated, the molecules and methods of the present invention are made and employed using conventional techniques of chemistry, biochemistry, and molecular biology, which are well-known and within the capabilities of a person skilled in the art to which this invention belongs (for example, see [15–20]). Unless defined otherwise, all technical and scientific terms used herein have the same meaning as commonly understood by one skilled in the art to which this invention belongs. The term "nanomachine" as used herein is a nanometer-scale molecular structure which functions as a machine; that is, as a device that transmits or modifies energy, or as a combination of rigid or resistant bodies having definite motions and capable of performing useful work (see the definitions of "machine" in [21], p. 1289; and in [22], p. 951). Similarly, the term "nanomotor" as used herein is a nanometer-scale molecular structure which functions as a motor, in that it converts chemical energy into mechanical energy, causing movement (definitions for "motor" are found in [21], p. 1417; and in [22], p. 1046). Analogously, the term "molecular switch" as used herein is a molecular complex or assembly which functions as a switch; e.g., it indicates one of several alternative states or conditions that have been chosen (see "switch" as defined in [21], p. 2149; and in [22], p. 1593). The preferred methods and materials are described herein; however, any methods and materials similar or equivalent to those described herein can be used in the practice or testing of the present invention.

Hybridizing Oligomers

In the embodiment of the invention portrayed in FIG. 1 and described below, the hybridizing motor, fuel, and removal strands are DNA oligomers. One skilled in the art would appreciate that the methods of the present invention can be practiced successfully using any of the known types of chemical oligomers which hybridize specifically to oligomers having complementary subunit sequences to form stable double-stranded complexes. The statement that an oligomer hybridizes specifically to another oligomer is intended to mean that a portion of a first oligomer comprising a subunit sequence complementary to a subunit sequence in a second oligomer binds by Watson-Crick base-pairing to the complementary portion of the second oligomer to form a stable double-stranded complex, under hybridization conditions that are sufficiently stringent that oligomer molecules having fewer bases complementary to, or forming less stable duplex structures with, the second oligomer do not also hybridize to the second oligomer and form stable double-stranded complexes. The hybridization may involve only a region of the molecules involved (preferably at least 3, and more preferably at least 8 base pairs) and need not produce a fully double-stranded molecule (i.e., there may exist regions of one or both molecules in the hybridized pair which are not complementary). The term complementary as used herein refers to the ability of two molecules to hybridize under standard conditions; however, it is preferred that oligomer sequences intended to be complementary according to the invention be designed to produce base-pairing between at least 90%, preferably 95%, and more preferably all, bases of the complementary portions. Selection of parameters such as the lengths and nucleotide sequences of the complementary portions of the different oligomers, the number of base mismatches in the hybridizing sequences to be tolerated or introduced by design, and the conditions used in hybridization and wash steps, so that the oligomers hybridize specifically to their counterparts, is well within the capabilities of a person of ordinary skill in the art (e.g., see chapter 11 of [15]). As used herein, the term oligomers refers to DNA or RNA oligonucleotides, DNA or RNA oligonucleotide analogs, or a combination of DNA and/or RNA oligonucleotides and DNA and/or RNA oligonucleotide analogs, which are used as hybridizing motor, fuel, and removal strands in the present invention. The RNA or DNA oligonucleotide analogs employed for the present invention can be oligomers in which from one to all nucleotide subunits are replaced with a nucleotide analog to confer desired properties such as increased detectability, altered hybridization affinity, and resistance to degradation by a nuclease. Such oligonucleotide analogs include but are not limited to oligomers comprising 2'-O-alkyl ribonucleotides, phosphorothioate or methylphosphonate internucleotide linkages, peptide nucleic acid subunits, and nucleotides modified by attachment of radioactive or fluorescent groups, catalytic moieties, groups which cross-link to other macromolecules, groups which intercalate into nucleic acids, or groups which alter the electric charge or hydrophobicity of the oligomers. Methods for making and using oligonucleotides and oligonucleotide analogs such as those listed above are well known to those skilled in the art of making and using sequence-specific hybridizing oligomers. Depending on the purpose for which the oligomers are used, e.g., as motor, fuel, or removal strands, and on the relative and absolute rates of strand association and dissociation desired, the oligomers of the invention can be n-mers of from about 10 up to about 20, 30, 50, or 100 or more subunits, e.g., nucleotides, in length; preferably about 10 to about 50 nucleotides in length, and even more preferably about 10 to about 30 nucleotides in length. Those skilled in the art would appreciate that in order for the oligomers to hybridize specifically to form stable double-stranded complexes, the oligomers should be at least about 6–8 nucleotides in length. Those skilled in the art also appreciate that the specificity and affinity with which oligomers hybridize to each other are determined, in large part, by the length, nucleotide sequence, and chemical structure of the oligomers, and so are able to select structural parameters of the oligomers employed in the present invention that are appropriate for their intended use. For example, the subunit sequences of the different motor, fuel, and removal oligomer strands of the invention can be selected so that the oligomers do not comprise self-complementary sequences that stabilize folding of said oligomers into hairpin structures which interfere with formation of inter-strand duplexes. Additionally, the subunit sequences of the oligomers, and the chemical composition of the reaction solution, can be selected so that the melting temperatures (Tm) of the double-stranded complexes formed by hybridization of complementary portions of the motor and fuel strands, or of the fuel and removal strands, are all within a selected temperature range, e.g., in the range of a selected Tm plus or minus about 5 degrees C, for more efficient control of oligomer hybridization and release (see, for example, p. 11.48 of [15]).

Obtaining the Oligomers

The present invention employs multiple sets of large numbers of different oligomers, for example, DNA oligonucleotides, having specified lengths and nucleotide sequences. The oligomers of the present invention can be made by well-known methods that are routinely used by those skilled in the art of synthesizing oligonucleotides and/or oligonucleotide analogs (for example, see [18, 19, and 23]).

A Molecular Motor Controlled by Hybridizing Oligomers

Figure 1B:
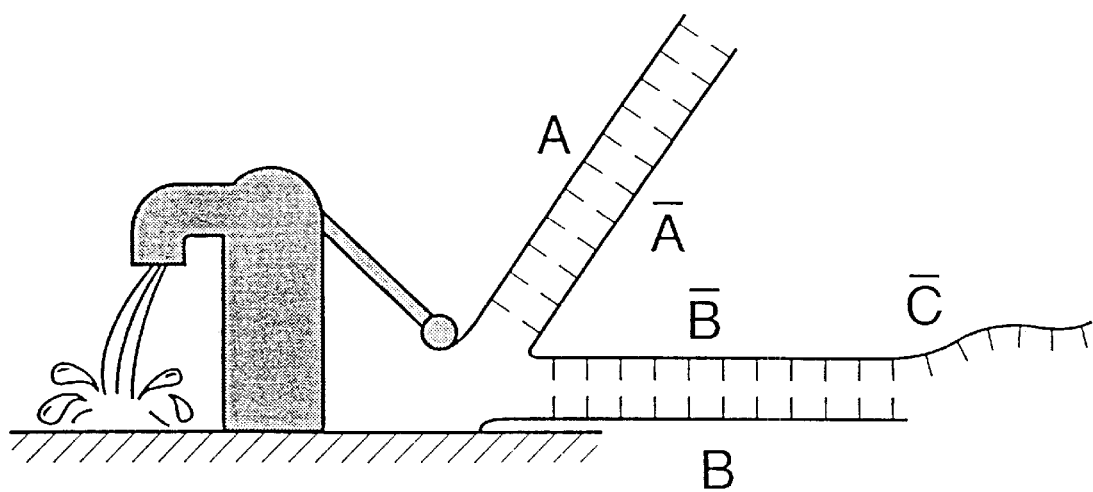
Figure 1C:
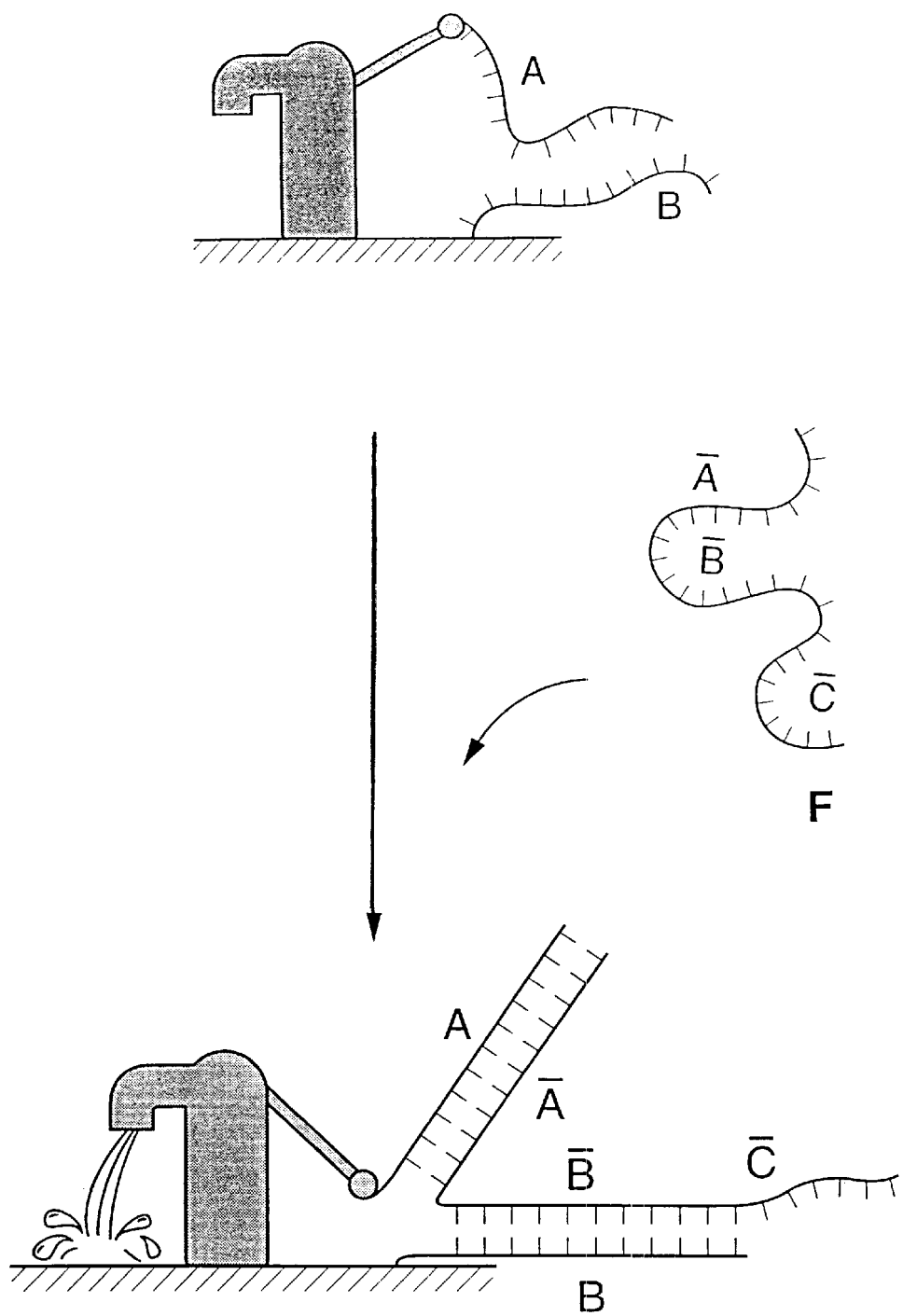
Figure 1D:
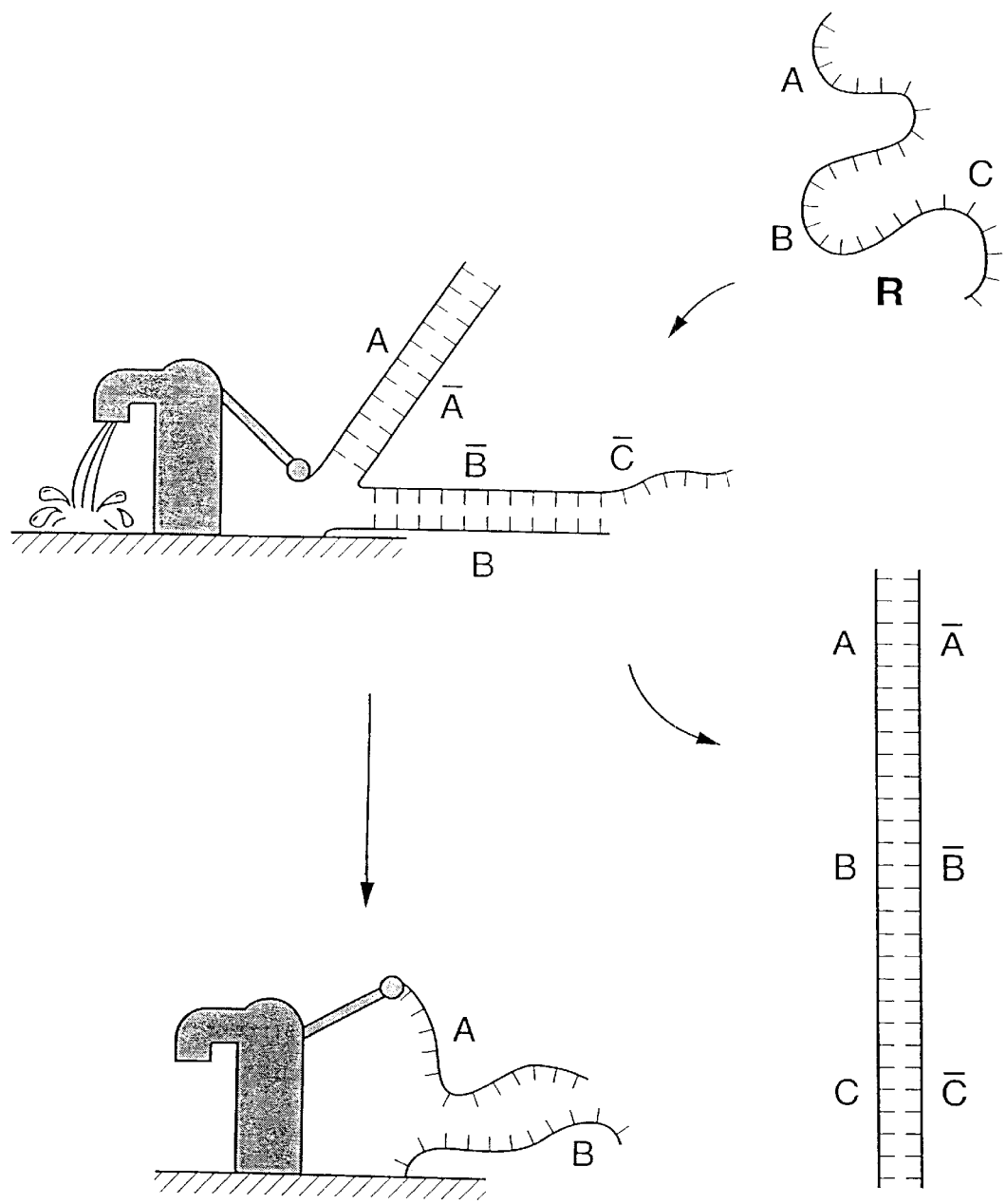
Figure 1E:
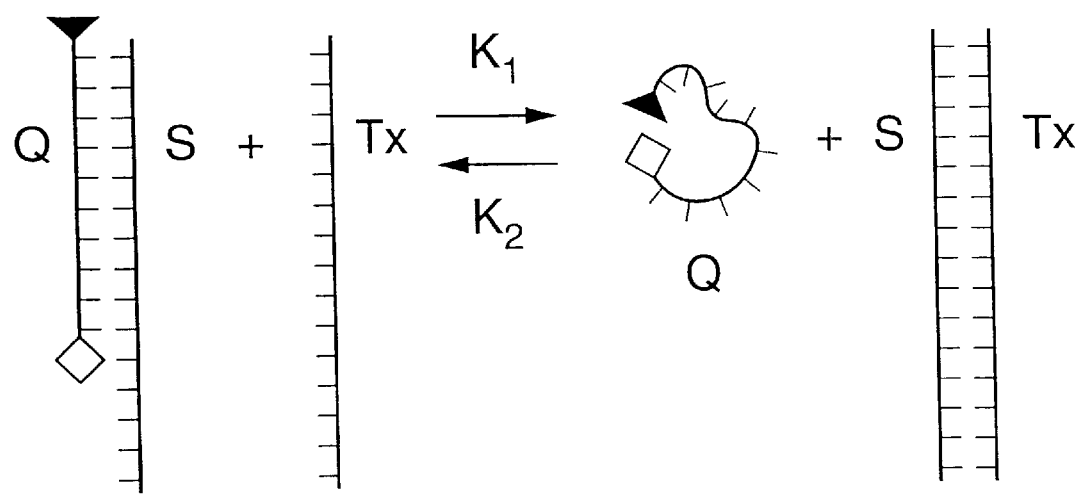
FIG. 1(e): A chemical reaction is studied to measure the rate of toehold-mediated strand exchange. The diamond and the filled triangle denote dye molecules covalently linked to the ends of DNA strand Q. When Q is bound to S the dye molecules are separated sufficiently far so that no fluorescence quenching occurs. When Q is in solution the dye molecules are brought close to each other resulting in fluorescence quenching. This phenomenon is used to monitor the kinetics of the strand exchange process.
Figure 2A:
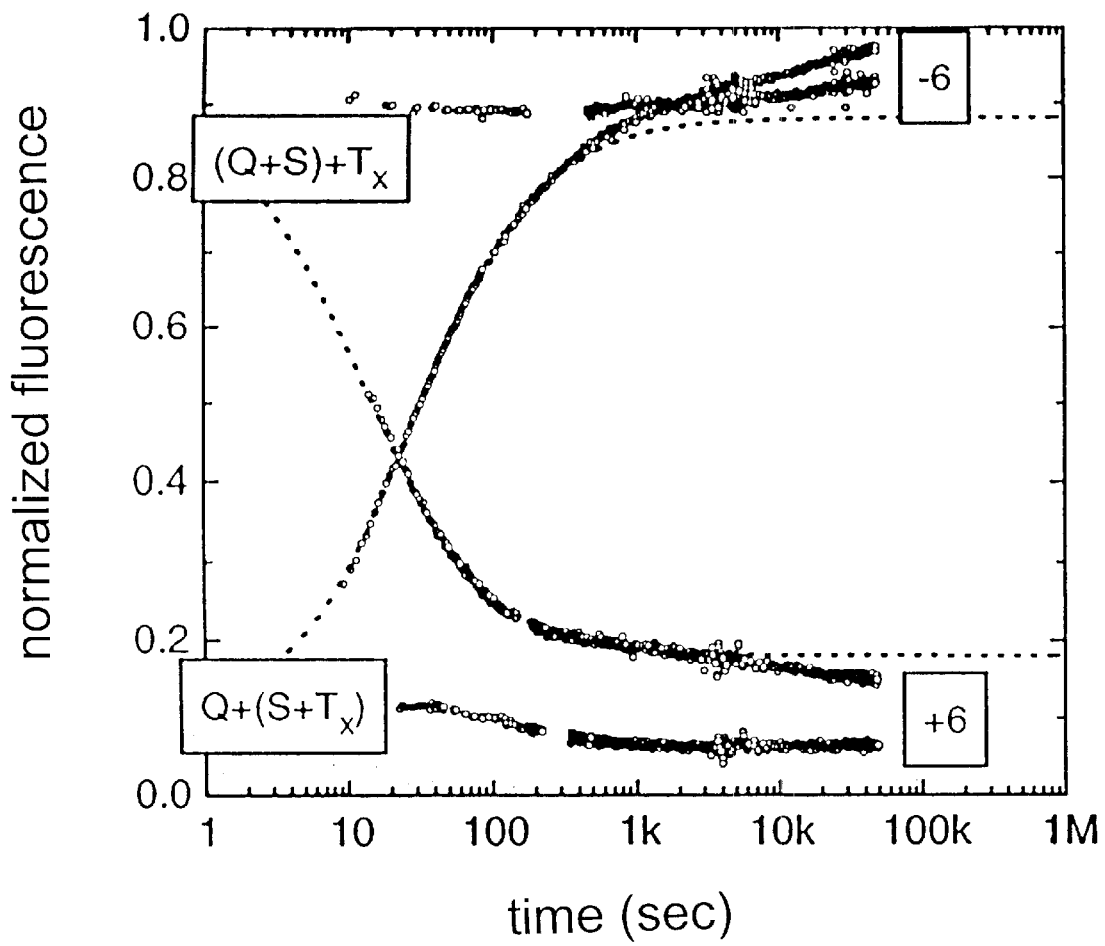
FIGS. 2(a), 2(b), and 2(c) each represents a single run in which four samples were monitored. The order in which reactants were added is indicated in the boxes on the right side of the figure frames. The length of the toehold region is indicated in the boxes on the left side of the figure frames.
Figure 2B:
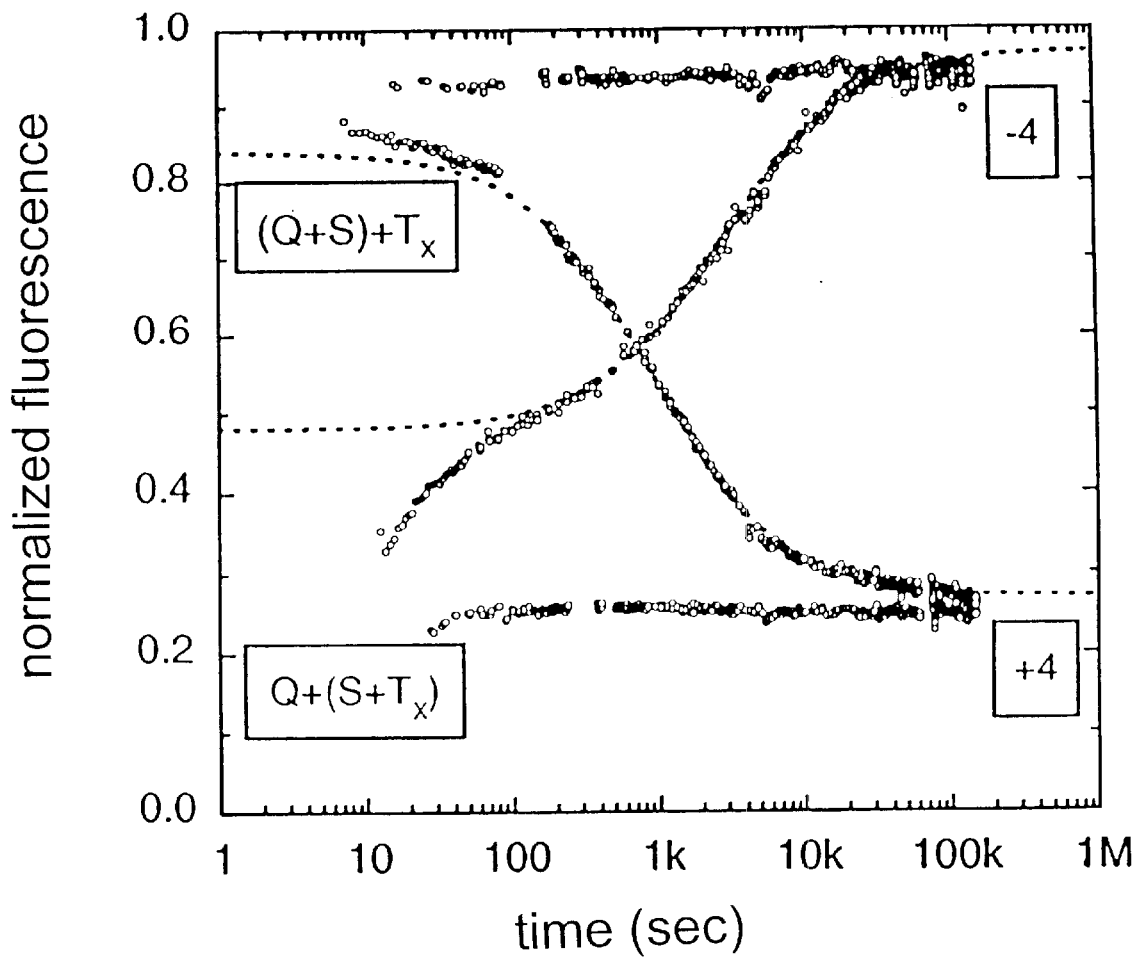
Figure 2C:
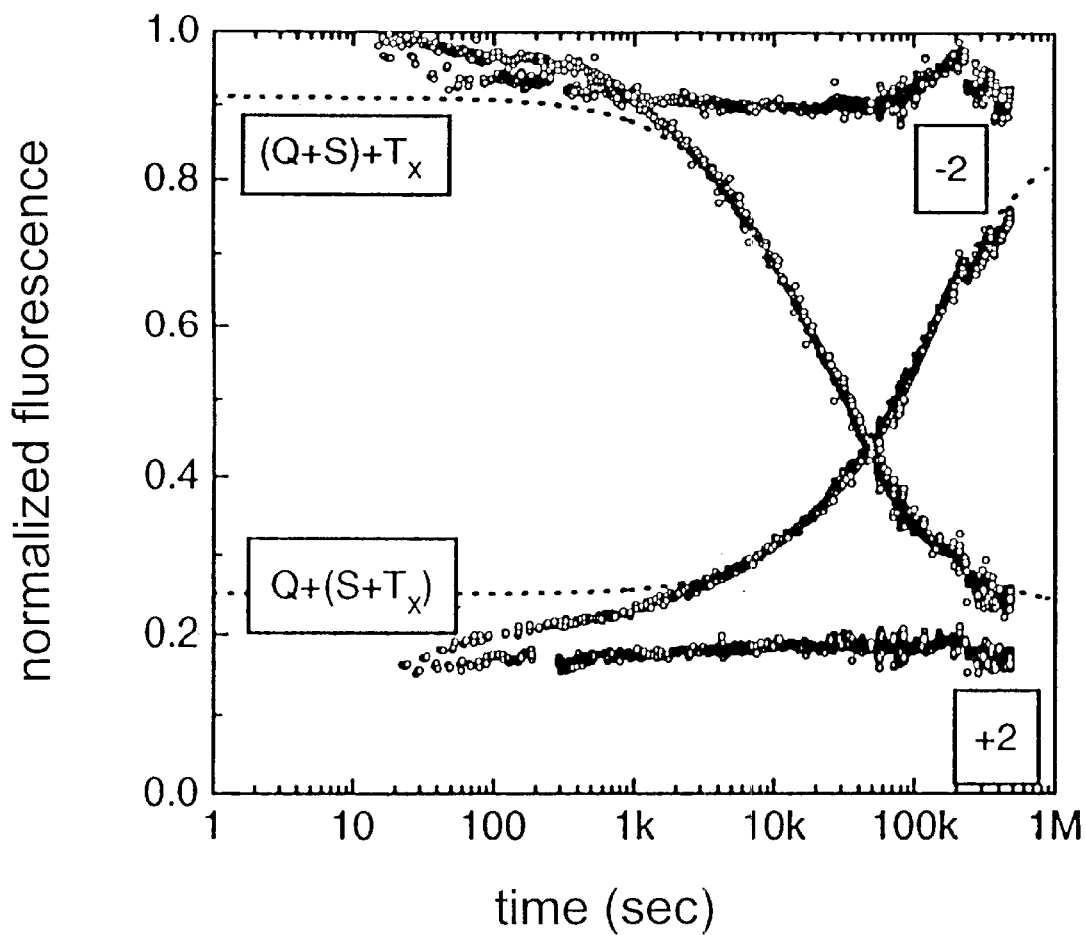
Figure 2D:
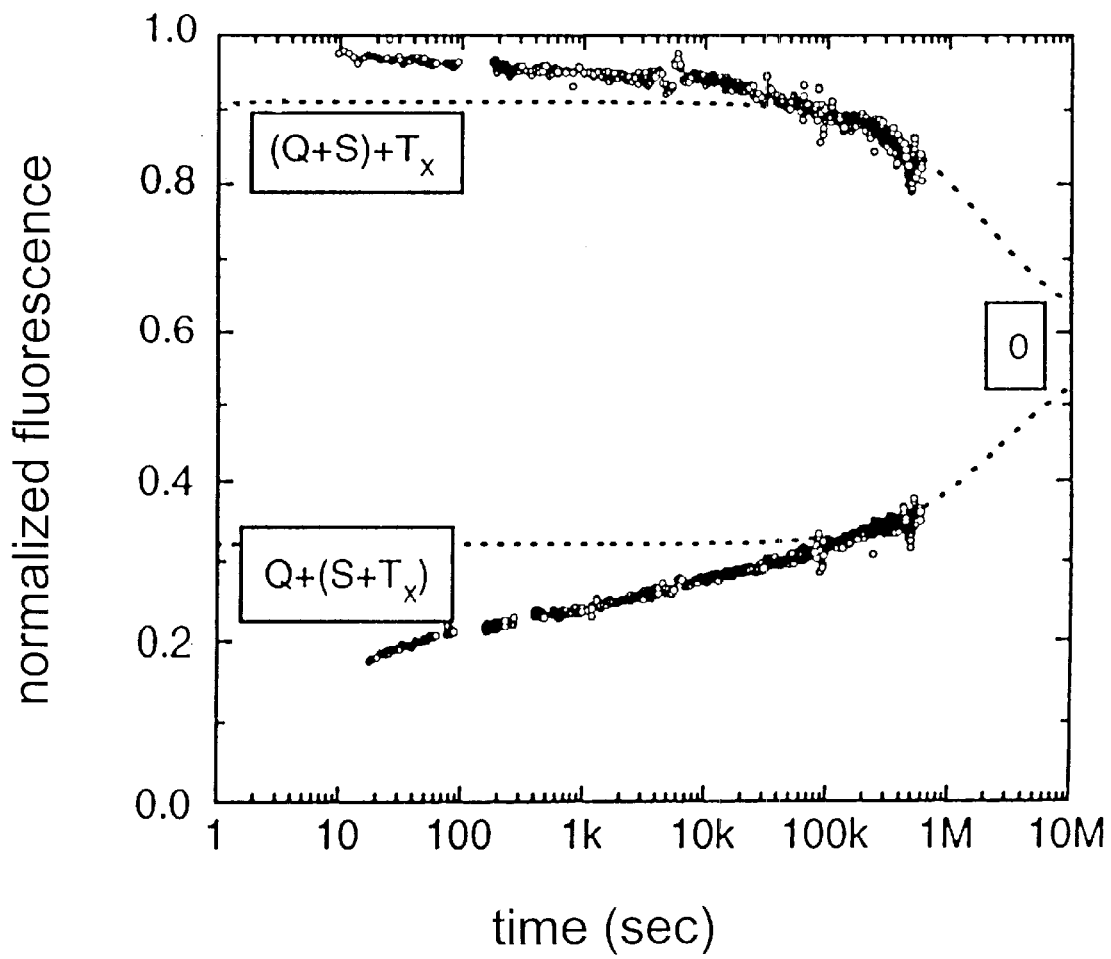
FIG. 2(d) shows data from a run in which the toehold length is zero. The dashed curves are fitted to the data of the theory embodied in Equation (4).

To illustrate how a molecular motor powered by DNA fuel could be devised, some strands of DNA are schematically depicted in FIGS. 1(a) and 1(b) as operating the handle of a fluid pump. In FIG. 1(a) the pump is depicted in its relaxed configuration. A strand of single-stranded DNA having the nucleotide sequence A is covalently bonded at one end to the pump handle. Also, a strand of single-stranded DNA of sequence B that is not complementary, to A is covalently bonded at one end to the substrate, or "floor". These two strands are here referred to as the "motor" strands. The power stroke of the pump is initiated by supplying the system with a strand of DNA, referred to as the "fuel" strand, whose nucleotide sequence consists of the concatenation of the nucleotide sequences $\overline{A}$, $\overline{B}$, and $\overline{C}$. Here and throughout the manuscript the overbar is used to denote the complement of a sequence. The $\overline{A}$ region of the fuel strand hybridizes:with the motor strand covalently linked to the pump handle, and the $\overline{B}$ region hybridizes with the motor strand covalently attached to the floor. As the strands zip together the pump handle is pulled down as shown in FIG. 1(b). The free energy $\Delta G_M$ of hybridization of $\overline{A}$ with A and $\overline{B}$ with B is, in principle, available to pull the pump handle down. Design considerations dictate how much of this energy can be tapped. In particular, for the device depicted in FIGS. 1(a) and 1(b), strand A and the $\overline{A}$ region of the fuel strand should be chosen long enough so that, even if the fuel strand is fully hybridized with B, region $\overline{A}$ of the fuel strand can still reach strand A. A similar consideration applies for strand B and the $\overline{B}$ region of the fuel strand. Thus, for this device less than half of the bonds formed during hybridization will participate in pulling the pump handle down. $\Delta G_M$ depends on the nucleotide sequences of the DNA strands involved. Methods taking account of nearest neighbor effects exist for calculating $\Delta G_M$ [24–26], but a useful value for rough estimates is $-6 \times 10^{-2}$ eV per nucleotide. Actual values can vary a factor of two above or below this value. Since the spacing between nucleotides is 3.4 Å, this motor could develop forces on the order of 30 pN, which is 3 to 10 times larger than the forces developed by biological molecular motors [27–33]. The fuel strand is removed by a strand of DNA referred to as the "removal" strand. Its nucleotide sequence consists of the concatenation of the sequences, A, B, and C, that is, the removal strand is complementary to the fuel strand. The purpose of the region $\overline{C}$ on the fuel strand is to provide a nucleation site for hybridization to which the removal strand can bind via complementary pairing of nucleotides. Such a single-stranded region which serves as a nucleation site for hybridization of the removal strand is referred to herein as a "toehold." Once it hybridizes to the toehold sequence, the removal strand competes with the motor strands B and A for binding with the fuel strand, thus eventually removing the fuel strand from the motor strands. The duplex formed by the fuel strand and the removal strand can be viewed as spent fuel. With the fuel strand released from the motor strand the pump handle is free to move back to its relaxed position depicted in FIG. 1(a).

Since the fuel strand and removal strand can hybridize with each other directly, the molecular motor must be operated in a clocked manner in which the fuel strand and removal strand are added in serial fashion in order to obtain cyclical changes in configuration changes and the concomitant generation of force. This provides a degree of control not possessed by biological molecular motors which are generally free-running. Due to thermal fluctuations, there is a finite rate for the fuel strand to spontaneously dissociate from the motor strand. A dissociation rate of $1.1 \times 10^{-2}$ sec$^{-1}$ at 30.5° C. for 10-mers has been reported by Morrison and Stols [1]. An extrapolation of their data [1] for 20-mers yields a dissociation rate of $1 \times 10^{-10}$ sec$^{-1}$ at 30.5° C. Hence, even with relatively short strands of order 20 or 30 nucleotides, it is easy to get into a regime where spontaneous dissociation is negligible.

Supporting Structures

The reversible hybridization of the fuel and motor nucleic acid strands causes these strands to undergo a transition from relatively flexible single-stranded oligomers to much stiffer and less flexible double-stranded oligomers. This transition between flexible and rigid structures provides the driving energy which enables the molecular motor of the present invention to generate a "power stroke" to perform useful work. Accordingly, a molecular motor of the present invention can be physically coupled to any nanodevice that operated by directed application of force of the order of 30 pN. Alternatively, a nanodevice of the present invention can be employed independently as a molecular switch which is reversibly closed and opened by the reversible hybridization a fuel oligomer to a motor strand, as exemplified in FIGS. 1(a) and 1(b). In order to capture and use the energy of the single- to double-strand structural transition of the motor and fuel oligomers, at least one of the motor oligomers is securely attached to an anchoring molecular structure. The molecular structure to which the motor oligomer is attached can be a soluble or anchored macromolecule, e.g., a component of the nanodevice itself, or it can be a fixed substrate that is separate from the nanodevice. A variety of different designs and materials are available for preparing a controllable, 2-state nanodevice of the present invention. In a preferred embodiment, at least one of the motor oligomers is attached to a soluble macromolecule or macromolecular complex comprising one or more natural or nonnatural nucleic acid, nucleic acid analog, polypeptide, carbohydrate, lipid, or nonnatural structural molecules, or a combination of these.

In an embodiment exemplifying the present invention, each of two motor strands can be attached to separate, extended, relatively inflexible, rod-like molecular structures that are linked together at one end by a flexible "hinge" moiety as "handles" of a pair of molecular "tongs" or "tweezers," as described in Example 1, so that binding of the fuel strand causes the ends of the rod-like arms to be drawn together, thereby closing the tongs. As used herein, the term "rod-like" refers to a structure that is relatively rigid, stiff, or inflexible. The tongs are then returned to an open, relaxed configuration by toehold-mediated removal of the fuel strand from the motor strand. Examples of rod-like molecular structures that can be used as the arms of the tongs include a double-stranded nucleic acid, a triple-stranded nucleic acid, a protein alpha helix, and a protein triple helix (as in collagen), as well as a non-natural, synthetic molecular structure. In contrast, a single-stranded nucleic acid or a polypeptide random coil is relatively flexible, and is therefore not "rod-like". Fluorophores can be attached to one or more portions of the nanomachine whose motion is controlled by hybridization of the fuel strand to the motor strand(s); for example, to the "arms" of the molecular tongs, or to either the motor or fuel strand, in such a manner that binding of the fuel strand to the motor strand results in a change in the intensity of fluorescence of the fluorophore, thereby providing a detectable signal indicative of the current configuration of the nanomachine. An embodiment of such a nanoswitch is demonstrated using TET and TAMRA dyes in Example 1. However, Example 1 is not to be taken as limiting; one skilled in the art would know of many different combinations of quenchable fluorophores that could be used in like manner to generate variations in fluorescence intensity, through fluorescent resonance energy transfer, that operate to signal changes in configuration of a nanodevice according to the present invention. For example, the quencher DABCYL (4-[4'-dimethylaminophenylazo] benzoic acid) can be used in combination with any of the fluorophores Coumarin, EDANS Fluoroscein, Lucifer yellow, BODIPY, Eosine, Texas Red, or Tetramethylrhodamine [68] to generate a quenchable signal in such manner. Such a nanomachine can operate as a reversibly controllable switch or signalling moiety, with strand-displacement permitting reversible-control at a constant temperature. Binding of the fuel strand to the motor strand would put the switch in the "on" position, and toehold-mediated displacement of the fuel strand by the removal strand provides a means for returning the switch to the "off" position. Detection of a configuration-dependent change in fluorescence intensity is a rapid and efficient means for identifying the physical state of such a nanoswitch of the present invention.

The motor oligomer(s) can be attached to a two-dimensional molecular array or surface, such as the "floor" shown in FIGS. 1(a) and 1(b). In a preferred embodiment, motor strands are attached to a two-dimensional supporting structure made up of interconnected "tiles" or "modules" consisting of double-stranded DNA molecules held together by double-crossover junctions, with single-stranded DNA extensions of adjacent "tiles" hybridizing together to connect the tiles into a lattice, as described in [11]. By selecting appropriate nucleotide sequences for the single-stranded DNA extensions, the flat DNA modules can be made to assemble in a pre-determined pattern to produce a complex, non-repetitive, two-dimensional lattice that can serve as a template for the precise positioning of DNA nanomachines of the present invention, and other nanodevices. This can be accomplished, for example, by providing each type of DNA "tile" or module with one or more additional single-stranded DNA side chains or side loops with unique DNA sequences to which complementary single-stranded DNA regions of a molecular machine could hybridize. The unique single-strand DNA extensions on each type of module allow different types of molecular machines to be positioned precisely with respect to each other; e.g., for assembling a "nanofactory" of multiple, interacting molecular machines.

The motor oligomer(s) can also be attached to a two-dimensional substrate that is a rigid material such as silica, silicon, glass, crystalline Al $_2$O$_3$ ("synthetic sapphire"), beryllium oxide, or a solid substrate coated with a noble metal such as gold. Alternatively, the substrate can be distributed in three dimensions, such as in a gel, a fibrous or granular matrix, or in a porous solid; for example, the substrate may be a polymer such as those used to support affinity groups for chromatography. The substrate polymer may be rigid or flexible, randomly coiled or organized, and of natural composition, such as DNA or polypeptide, or of nonnatural composition.

Methods for obtaining nucleic acid oligomers attached to supporting molecules or substrates in a manner suitable for the present invention are well known. Such methods include in situ synthesis of oligomers attached at their 3' ends to functional groups positioned on the supporting structures (for example, see [34] col. 4, line 67 to col. 10, line 35; [35] col. 23, line 3, to col. 25, line 18; and [36] col. 17, lines 21–63). Alternatively, pre-synthesized oligomers can be chemically attached to the supporting structures; e.g., by derivatizing the oligomers or the attachment sites, and then allowing the oligomers to react with the chemical groups on the surfaces of the supporting structures, or by allowing biotinylated oligomers to bind to streptavidin groups attached to the supporting structures or surface sites (see [34] col. 1, line 18 to col. 3, line 13 and col. 6, line 21 to col. 10, line 35; [37] pages 607–609; [38] col. 13, lines 2–9; and [39] pages 27–29). In a preferred embodiment, motor strands or the nanomachines to which they are joined are tethered to a supporting molecular structure with uncharged spacer groups ([36] col. 11, line 49, to col. 13, line 45; and [40] pages 5022–24). The use of such spacer groups to tether nucleic acid oligomers to a solid substrate is known to increase hybridization efficiency of the oligomers, relative to oligomers attached directly to the substrate. ([39] page 29).

Using the Invention

Key to the operation of the motor depicted in FIGS. 1(a) and 1(b) is strand exchange, which allows the removal of the fuel strand after the power stroke has been completed. Toehold-mediated strand exchange, which provides the energy for the present invention, is mechanistically much simpler than the processes of nucleic acid strand exchange in biological systems, which are mediated by proteins such as recA [41].

Those skilled in the art would appreciate that the nucleic acid "two-stroke engine" of the present invention can be operated in combination with other types of nanodevices to produce more complex nanomachines. For example, the 2-state nanomotor of the present invention can be linked to, or in contact with, a nanomachine which is operated by repetitive application of a force of the order of 30 pN, to provide the power needed for the operation of said nanomachine.

The present invention can also be used as a controllable nano-scale extensor arm; hybridization of the fuel strand to at least one motor strand causes the motor strand to extend as a rigid arm. A selected chemical moiety can be attached to the motor or fuel strand so that when the extensor arm extends, the chemical group becomes precisely positioned relative to other chemical structures in proximity to the extensor arm. Toehold-mediated removal of the fuel strand returns the motor strand(s) back to its flexible single-stranded form, so that the attached molecular group is no longer held in the fixed position. The molecular group that is attached to a motor or fuel strand operating as a controllable extensor arm in this fashion is selected according to the needs of the user. For example, a dye moiety such as TAMRA can be attached to a movable portion of a nanomachine, or to the motor or the fuel strand, so that hybridization of the fuel and motor strands produces a relatively rigid double-stranded "rod" or "arm" that stably positions the TAMRA moiety adjacent to a TET moiety that is positioned nearby, thereby quenching fluorescence of the TET moiety. The TET moiety might be attached to a separate portion of the nanomachine, to a motor or fuel strand, to a separate nanodevice, to the substrate, etc. Removal of the fuel strand returns the motor strand to its flexible, single-stranded state, so that association of the TAMRA moiety with the TET group is reduced, and the quenching of TET fluorescence is relieved. Those skilled in the art would recognize that other chemical interactions that depend on proximity of reactive groups, such as catalytic action of an enzyme on its substrate, cleavage of a nucleic acid substrate by a ribozyme, chemical crosslinking or cleavage of a nucleic acid, etc., can be directed or controlled in a similar manner using the present invention.

As discussed above, those skilled in the art would appreciate that reversible hybridization of the fuel and motor nucleic acid strands according permits the present invention to operate as a 2-state molecular switch that indicates a state or condition of a system. Also noted above, the nucleotide sequences of the controlling oligomers of such a switch can be selected so that switch operation is temperature-sensitive. Those skilled in the art recognize that a molecular switch according to the present invention can be used to store data; for example, in one state the switch can represent 0, and in the other state it can represent 1. An array of such switches, controlled by fuel and removal strands having selected nucleotide sequences, can be operated as a molecular abacus or a digital computer.

Assays for Selecting Oligomer Parameters Giving Desired Control Characteristics In order to select the oligomer parameters of length and subunit sequence to obtain hybridization affinities giving desired degree of control of the invention, it is helpful to have an understanding of the chemistry and physics of the operation of the invention. Accordingly, important physical aspects of the invention, as portrayed schematically in FIGS. 1(a) and 1(b), are described below. For simplicity, only the process of removing the fuel strand from the B motor strand is considered, since the removal of the fuel strand from the A motor strand is a continuation of the same physical process.

In the discussion which follows, a single motor strand is denoted by M, a fuel strand is denoted by F, and a removal strand is denoted by R. The reactions under consideration are thus $$MF + R \underset{K_2}{\overset{K_1}{\rightleftharpoons}} M + FR \tag{1}$$

where $K_1$ and $K_2$ are the forward and backward rate constants. For simplicity, the reaction that is considered, and for which the reaction kinetics measurements are made, is one in which the MF duplex is not under stress. In a DNA-based motor, such as that depicted in FIGS. 1(a) and 1(b), the MF duplex will generally be under stress that will enhance the forward reaction rate $K_1$ and suppress the backward rate $K_2$. Hence, measurement of the reaction kinetics under no-load conditions provides a lower bound on the rate with which the molecular machines can be cleared of their fuel strands. Under no-load conditions, the ratio of the rate constants is given by $$\frac{K_2}{K_1} = e^{\Delta G/kT} \tag{2}$$

where $\Delta G$ is the free-energy change in duplex formation for the toehold region. Under stoichiometric conditions, the ratio of the equilibrium concentration [MF] of motor strands duplexed with fuel strands to the equilibrium concentration [FR] of the removal strands duplexed with fuel strands is $$\frac{[MF]}{[FR]} = \sqrt{\frac{K_2}{K_1}} \tag{3}$$

The longer the toehold region is, the smaller the ratio $K_2/K_1$ of Eq. (3) becomes and, consequently, the smaller [MF]/[FR] becomes. Hence, one purpose of the toehold region is to drive the chemical reactions in the correct direction. Using the rough value for $\Delta G$ of $-6 \times 10^{-2}$ eV per nucleotide, one sees that even for a two-nucleotide toehold, the reaction is driven to 91% completion. The rate with which the reaction proceeds to completion can be calculated from $K_1$, $K_2$, and the concentration of the various DNA strands. In particular, for the case when the initial concentration of removal strands $[R]_0$ is equal to the concentration of duplex motor-fuel strands $[MF]_0$, and neglecting back reaction Eq. (1), the fraction of the motor strands which have had their fuel strands removed is given as a function of time by $$\frac{[M]}{[MF]_0} = \frac{K_1[R]_0 t}{1 + K_1[R]_0 t} \tag{4}$$

Half the motor strands M will have been stripped of their fuel strands by the time $t_{1/2} = 1/K_1[R]_0$. If the initial concentration of removal strands is in large excess over the motor-fuel strands, $[R]_0 \gg [MF]_0$ then the fraction of motor strands which have had their fuel strands removed is given as a function of time by $$\frac{[M]}{[MF]_0} = 1 - e^{-K_1[R]_0 t} \tag{5},$$

that is, the motor strands M are stripped of their fuel strands exponentially with time with an e-folding time of $\tau = 1/K_1[R]_0$.

It is recognized that single-stranded regions referred to herein as toeholds provide hybridization nucleation sites that enhance the rate of strand displacement [1–3]. Little is known about the dependence of the rate of strand displacement on the length of the toehold region. To have control over the operation of a nanomachine or molecular switch driven by toehold-mediated strand-displacement, it is necessary to know the rate with which a given removal strand associates with a toehold of selected structure in the reaction leading to removal of a fuel strand. Reaction kinetics measurements are described below which quantitatively exhibit this effect. The disclosed experimental measurements were based on the observation of hybridization via fluorescent dye quenching, a technique first described by Heller and Morrison [42] and subsequently widely used for the "Taqman" assay (Perkin-Elmer) as well as in other applications [43]. The measurements were performed in SPSC buffer [44] (50 mM sodium phosphate and 1 M NaCl at pH 6.5) at 20.0° C. The nucleotide sequences of the strands of DNA used in the experiments are listed in Table I. These oligonucleotides were purchased from Perkin-Elmer as high pressure liquid chromatography (HPLC) purified oligomers. The oligonucleotides were initially diluted in TE Buffer (2 mM TRIZMA base and 0.2 mM EDTA) to a nominal concentration of 25 $\mu$M, based on the manufacturer's measurements of the amount of DNA. The actual concentrations of the oligonucleotides were measured relative to a standard using both gel electrophoresis and fluorescence quenching titrations. The samples were prepared so that the reaction kinetics would proceed in SPSC buffer and 1 M NaCl. The concentrations of the different oligonucleotides were stoichiometric relative to each other to within ±7%. The concentration of each oligonucleotide in the reactions was 1.0±0.2 $\mu$M.

The chemical reactions carried out are shown in FIG. 1($e$). The "quenching" strand Q and a "toehold" strand $T_x$ were made to compete with each other for binding to the "straightening" strand S. The $T_x$ strands differ from each other in length, where x=±6, ±4, ±2, or 0 is the number of nucleotides in the toehold (See Table 1), allowing a range of toehold sizes to be explored.

TABLE 1

Oligonucleotide sequences
The 5' end of each sequence is at the left end.

| Name | Sequence |
|---|---|
| S | AGTACGGACACTAGCTGGATCTGAGGATTAGTA (SEQ ID NO.:1) |
| Q | TET-AACTAATCCTCAGATCCAGCTAGTGTC-TAMRA (SEQ ID NO.:2) |
| $T_{-6}$ | ACTAATCCTCAGATCCAGCT (SEQ ID NO.:3) |
| $T_{-4}$ | ACTAATCCTCAGATCCAGCTAG (SEQ ID NO.:4) |
| $T_{-2}$ | ACTAATCCTCAGATCCAGCTAGTG (SEQ ID NO.:5) |
| $T_0$ | ACTAATCCTCAGATCCAGCTAGTGTC (SEQ ID NO.:6) |
| $T_2$ | ACTAATCCTCAGATCCAGCTAGTGTCCG (SEQ ID NO.:7) |
| $T_4$ | ACTAATCCTCAGATCCAGCTAGTGTCCGTA (SEQ ID NO.:8) |
| $T_6$ | ACTAATCCTCAGATCCAGCTAGTGTCCGTACT (SEQ ID NO.:9) |

The Q strand of DNA is labeled with the dye TET at the 5' end and the dye TAMRA at the 3' end. When Q binds with S to form a duplex, the spacing between the dyes is 90 Å and TET exhibits nearly normal fluorescence. When Q is unbound in SPSC buffer, random coiling of the DNA and hydrophobic interactions bring the TET and TAMPA sufficiently close to each other that the TET is almost completely quenched. This dye quenching phenomena [1, 42, 43, 45] allows one to follow the reaction kinetics by determining the amount of unbound Q present as a function of time. An apparatus was assembled to allow the monitoring of the fluorescence of four samples simultaneously. The light source consisted of a 1 kW Xe arc lamp filtered at 450 nm (Rolyn Optics K45, stock number 66.2105) to drive the TET fluorescence. Using a beam splitter and split optical fibers, the light was directed at four separate vials housed in an aluminum block whose temperature was maintained at 20° C. by a temperature-regulated circulating water bath. The lamp intensity was monitored by measuring the scattered blue light from the vials through 450 nm, 40 nm bandwidth, filters (Ealing 42-5132). A separate 550 nm, 40 nm bandwidth, filter (Ealing 42-5306) and Si photo diode (EGG FND-100) for each vial was used to monitor the fluorescence. A shutter at the output port of the lamp was used so that the samples were only illuminated over the short intervals during which data was taken. The time between exposures was increased approximately logarithmically with time to keep dye bleaching at a negligible level. FIG. 2 shows the normalized fluorescence intensity $$F_n = \frac{F - F_Q}{F_{QS} - F_Q} \quad (6)$$

as a function of time for various runs. Here F is the measured fluorescence of the mixture, $F_Q$ is the fluorescence of strand Q alone, and $F_{QS}$ is the fluorescence of a stoichiometric mixture of S and Q. $F_Q$ and $F_{QS}$ were measured before the beginning of each run as the ingredients were successively added. The quenching ratio $F_{QS}/F_Q$ was typically 8. As shown in FIGS. 2($a$), 2($b$), and 2($c$), the following four combinations of mixtures were monitored during the same run:

(1) (Q+S)+$T_x$, which denotes that Q and S are allowed to hybridize first and then $T_x$ is added; (2) Q+(S+$T_x$), which denotes that S and $T_x$ are allowed to hybridize first then added to Q; (3) (Q+S)+$T_{-x}$; and (4) Q+(S+$T_{-x}$). The reaction associated with each curve is indicated in the boxes on the left side of each figure frame. The toehold size x for each curve is indicated in the boxes on the right side of each figure frame. Typically, fluorescence measurements for the first 10 seconds of a run are missing because of the time involved in mixing and loading the sample. A typical run lasts several days. The dashed lines represent fits of the theory given by Eq. (4) to the data, assuming that the steepest portions of the curves represent true stoichiometric second order kinetic behavior. The data agree with Eq. (4) quite well over three decades in time. Deviations, particularly at late times, are attributed to instrument drifts resulting from the aging of the Xe light source. As the Xe light source ages, the light intensity distribution across the light beam changes. This leads to changes in the intensity distribution of the light illuminating the sample cells. Since the fluorescent light and the scattered light come from different portions of the sample vials, this leads to errors in determining the concentration of free Q molecules which show up as long time drifts. Deviations at early times, such as for the x=−4 case, are attributed to the presence of DNA strands having errors in the nucleotide sequence. The pairs of curves for each toehold size x show that the reactions in the forward direction proceed to near completion while the reactions in the backward direction proceed hardly at all.

FIG. 2($d$) shows the reaction kinetics data for the case when there is no toehold. Because of the finite lifetime of the Xe arc lamp it was not possible to follow this reaction to near completion without severe perturbations to the measurements. The dashed curves again represent a fit of stoichiometric second-order kinetics to the longest time portion of the data. Unequal time constants were allowed for the two curves, subject to the constraint that both curves approach an equilibrium value consistent with Eq. (3). Second-order kinetics does not fit the (Q+S)+$T_0$ or the Q+(S+$T_0$) data very well over the time interval for which we have data. We again attribute this to impurities and instrumentation drifts. The rate constants extracted for this case are likely to be lower bounds on the true rate constants. However, one does expect the zero toehold strand-exchange rate to be finite. Partial unzipping of DNA strands can facilitate strand exchange at rates much greater than the dissociation rate of the DNA duplexes by providing transient single stranded regions that act as toeholds. It is also possible that the dye molecules at each end of Q may provide a toehold by preventing perfect hybridization [1]. The mismatched pair of nucleotides (the A at the 3' end of S and the A at the 5' end of Q) may serve a similar role.

Figure 3:
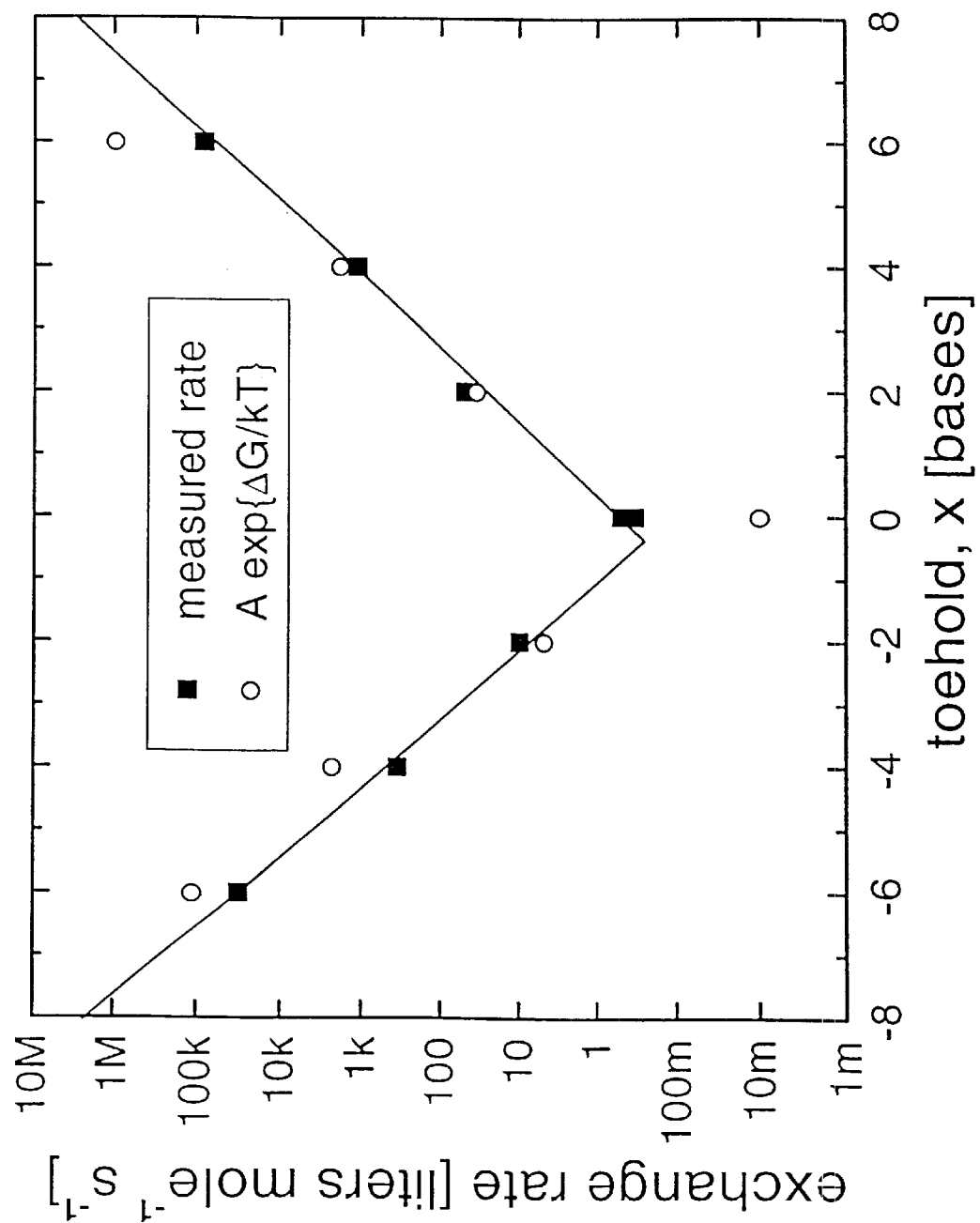
FIG. 3: Rate-constant data for toehold-facilitated strand exchange. The filled squares are the measured rate constants obtained from the reaction kinetics data of FIG. 2. The open circles are given by $Ae^{-\Delta G/kT}$ where $\Delta G$ is the change in the free energy resulting from strand exchange and A was taken to be 0.01 liter mole$^{-1}$ sec$^{-1}$. The straight lines are a plot of Equation (7) with $K_0$=0.27 liter mole$^{-1}$ sec$^{-1}$, $x_0$=−0.28 bases, and $\Delta G_{eff}$=51 meV/base.

The values of $K_1$ determined by fitting the theory of Eq. (4) to the steepest portions of the reaction kinetics data of FIG. 2 are plotted against toehold number x in FIG. 3 as filled squares. The open circles plot $Ae^{-\Delta G/kT}$, where A was taken to be 0.01 liter $mole^{-1}$ $sec^{-1}$ and $\Delta G$ is the free-energy change due to strand exchange, calculated according to SantaLucia et al. [25]. The lines are a fit to the data of the function $$K = K_0 e^{\Delta G_{eff}|x-x_0|/kT} \qquad (7),$$

where the fitting parameters are $\ln K_0 = -1.31 \pm 0.25$, $\Delta G_{eff} = 51 \pm 2$ meV/base, and $x_0 = -0.28 \pm 0.07$ bases. One sees that the data is asymmetric about x=0. This asymmetry also appears in the open circles and indicates that the effect may be partially due to the fact that the nucleotide sequence for the toehold x is different from that of toehold -x. For x=0, $\Delta G$=0. The fact that the measured rate constant (the two squares at x=0) is 40 times higher than the calculation (open circle) can be attributed to the partial unzipping of the ends of the duplex DNA due to thermal fluctuations. The maximum rate of strand exchange for our buffer conditions is limited by ordinary hybridization kinetics [1, 46, 47] to about $3 \times 10^6$ liter $mole^{-1}$ $sec^{-1}$. From extrapolating the data of FIG. 3, this limit should apply to toeholds of eight or more nucleotides.

In FIG. 4 the fluorescence from a run is shown in which stoichiometric amounts of S and $T_6$ are successively added so that Q is cycled between being duplexed with $T_6$ (the fluorescent state) and being single-stranded (the quenched state). This cycling mimics the cycling envisioned for the molecular motor in FIGS. 1(a) and 1(b), but in this case no useful work is being done by Q. The failure of the fluorescence to fully recover with each cycle is attributed to dilution effects and the build-up of impurity strands which have defects in their nucleotide sequences. Insufficient waiting time is not responsible for the incomplete recovery as is illustrated by the fact that when excess $T_6$ is added so that its concentration is twice (region E of FIG. 4) or four times (region F of FIG. 4) the stoichiometric value, the curve does not recover to the initial value at A.

The above-described examples demonstrate a large increase in the rate of DNA strand exchange in the presence of a toehold. In particular, we have observed an enhancement by factor of $6 \times 10^4$ in the rate of strand exchange when mediated by a toehold six nucleotides long for oligonucleotides whose overall length is 32 nucleotides. At a 1 mM concentration for the removal strands this would correspond to an e-folding time of 12 msec for fuel strand removal for the case when the removal strands are in large excess over the fuel strands. Hence, this mechanism can be used in devising DNA-based nanomachines driven by DNA hybridization and controlled at high rates by a fluidic device.

All publications and patent documents referred to herein are fully incorporated by reference.

EXAMPLE

This example demonstrates the construction of a new class of active nanostructure: a machine in which DNA is used not only as a structural material but also as a fuel. The specific embodiment exemplified below ia a molecular "tongs" or "tweezers"—a simple nanomachine constructed of DNA that uses DNA as a fuel.

A. Description of the Nanomachine

Single strands of DNA composed of complementary sequences of the bases adenine, cytosine, guanine and thymine (A,C,G,T) hybridize to form a stable duplex (double helix) bound together by hydrogen bonds between complementary base pairs (A-T and C-G). Our machine is prepared by mixing stoichiometric quantities of three strands, A, B and C, in SPSC buffer [52] at 20° C. to give a final concentration of 1 $\mu$M; the base sequences chosen for the three strands are given in Table 2 [53].

TABLE 2

Oligonucleotide Sequences

| Name | Sequence |
|---|---|
| A | 5' TGCCTTGTAAGAGCGACCAT CAACCTGGAATGCTTCGGAT 3' (SEQ ID NO:10) |
| B | 5' ATGGTCGCTCTTACAAGGCA CTGGTAACAATCACGGTCTATGCG 3' (SEQ ID NO:11) |
| C | 5' GGAGTCCTACTGTCTGAACTAACG ATCCGAAGCATTCCAGGTTG 3' (SEQ ID NO:12) |
| F | 5' CGCATAGACCGTGATTGTTACCAG CGTTAGTTCAGACAGTAGGACTCC TGCTACGA 3' (SEQ ID NO:13) |

Figure 5A:
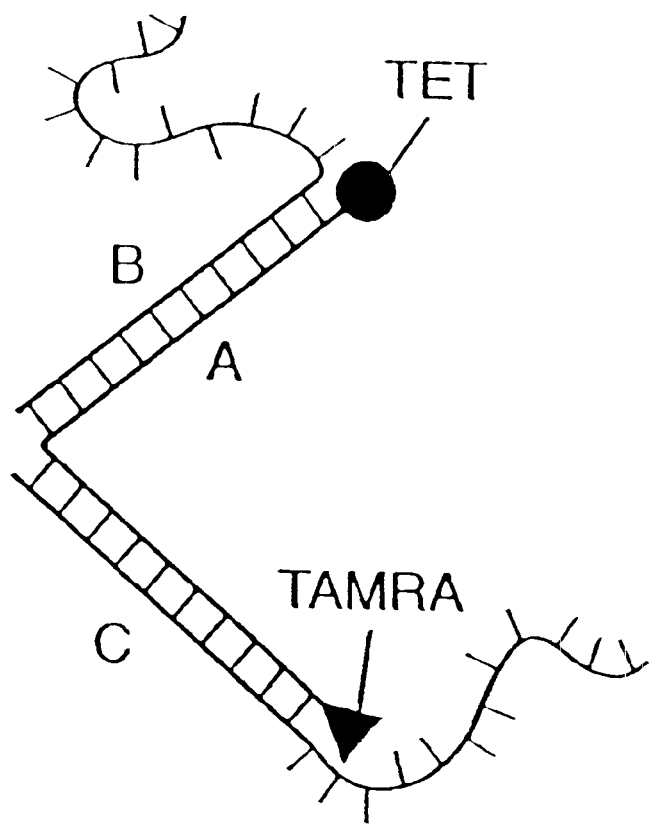
FIG. 5a: Schematic representation of a molecular "tweezer" nanodevice formed by hybridization of oligonucleotide strands A, B and C.
Figure 5B:
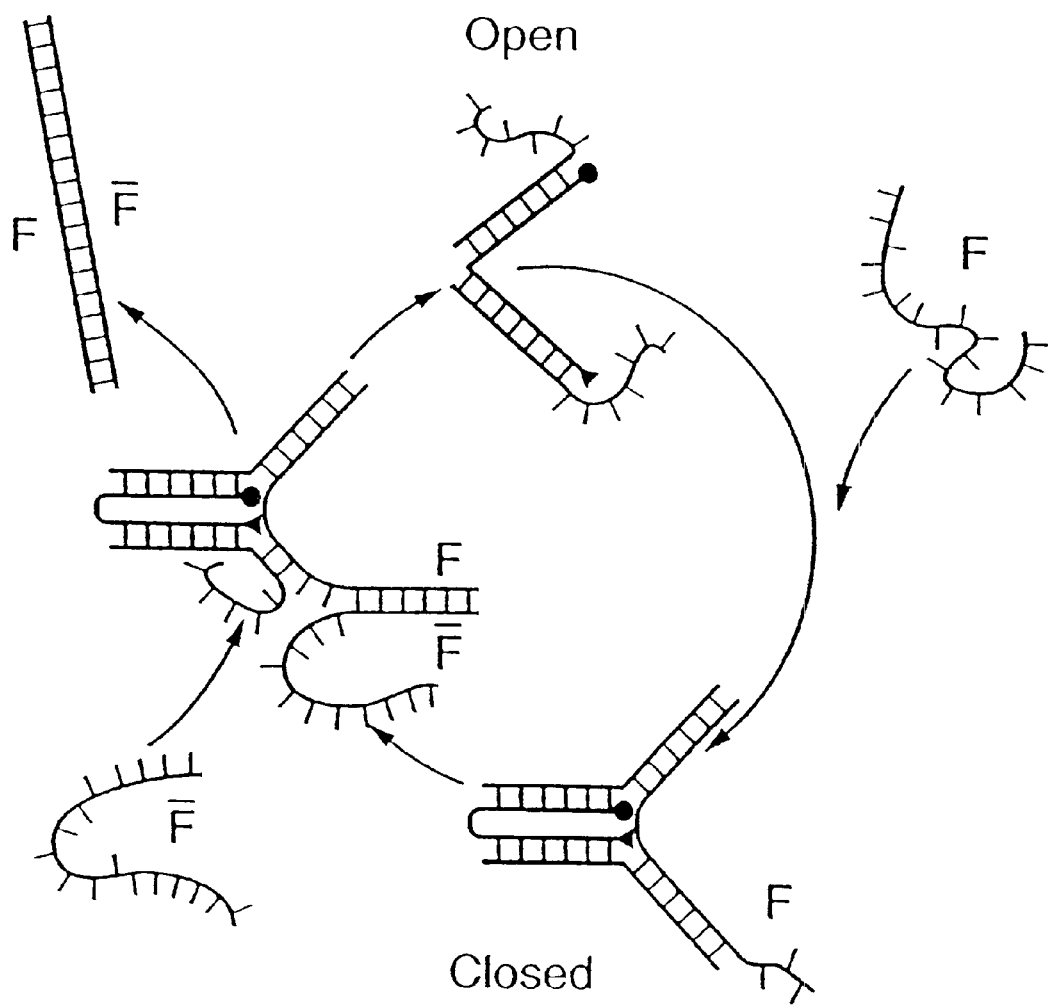
FIG. 5b: Schematic representation of reversible closing and opening of the molecular tweezers. Fuel strand F hybridizes with the dangling ends of strands B and C to pull the tweezers closed. Hybridization with the overhang section of F (single-stranded) allows strand $\overline{F}$ to remove F from the tweezers, forming a double-stranded waste product $F\overline{F}$ and allowing the tweezers to open.

The machine has the form of a pair of tweezers; its structure and operation are shown in FIGS. 5a and 5b. Strand A consists of two 20-base sequences which hybridize with complementary sequences at ends of strands B and C to form two stiff [54] arms; the hinge is formed where the ends of strands B and C abut (i.e. at a nick in the strand complementary to A). In the machine's rest state the remaining unhybridized 24-base portions of the 44-base strands B and C dangle floppily from the ends of the tweezers: double-stranded DNA has a persistence length of order 100 base pairs [54, 55] whereas at 1 M salt concentration single-stranded DNA has a persistence length ~1 nm [56, 57] or approximately three bases.

Strand A is labelled [53] at the 5' and 3' ends with dyes TET (5' tetrachloro fluorescein phosphoramidite) and TAMRA (carboxy tetramethyl rhodamine) respectively. When TET is excited by the 514.5 mn emission of an Argon ion laser it fluoresces with a peak emission wavelength of 536 nm; this emission is quenched by resonant intramolecular energy transfer from TET to TAMRA (a longer-wavelength dye whose absorption band overlaps the emission band of TET) with an efficiency that decreases rapidly as the distance between the dyes increases [58]. Fluorescence quenching of TET by TAMRA is accompanied by a corresponding increase in the fluorescent intensity of the TAMRA moiety. The quenching of TET fluorescence by TAMRA is used as an indicator [42] to titrate strands B and C against A; as half of A is straightened from a random coil by hybridization with B (or C) the mean separation between the dye molecules on A increases leading to a seven-fold increase in the fluorescence intensity. The cumulative effect of hybridization with both B and C is an eight-fold increase in fluorescence intensity in the rest state. The assembled tweezers are closed with fuel strand F and are opened with removal strand $\overline{F}$. The 56-base fuel strand F consists of two consecutive 24-base sections, which are complementary to the dangling ends of B and C, with an additional 8-base overhang section. FIG. 5b shows how fuel strand F hybridizes with the free ends of strands B and C, pulling the ends of the tweezers together. The average free energy change associated with the hybridization of a complementary base pair is −62 meV (−1.4 kcal mol$^{-1}$) [59] and the separation between base pairs in single-stranded DNA is 0.43 nm [60] giving an average closing force of about 10 pN, which is consistent with that required to pull apart double-stranded DNA [61]. This is at the upper end of the range of measured forces exerted by single-molecule kinesin [28, 29, 62] and myosin 31, 32] motors. Removal strand $\overline{F}$ is the complement of F; the additional free energy gained when the overhang (initially single-stranded) hybridizes with $\overline{F}$ ensures that addition of a stoichiometric quantity of $\overline{F}$ results in removal of F from the machine to form a double-stranded waste product F$\overline{F}$ and returns the tweezers to the open state. Hybridization between the fuel and removal strands occurs first at the exposed overhang [63] and then proceeds by branch migration [64], a random walk of the junction between the region of F newly hybridized to the removal strand $\overline{F}$ and the region still hybridized to the tweezer components B and C, that continues until both B and C have been completely displaced and the F$\overline{F}$ duplex diffuses away. The random walk occurs sufficiently quickly that the rate-limiting step in this strand-displacement reaction is the endothermic nucleation of a region in which complementary bases on the F and $\overline{F}$ strands are joined [47, 63, 65]: as a result, the measured second-order rate constants for opening and closing the tweezers are approximately equal.

Figure 6:
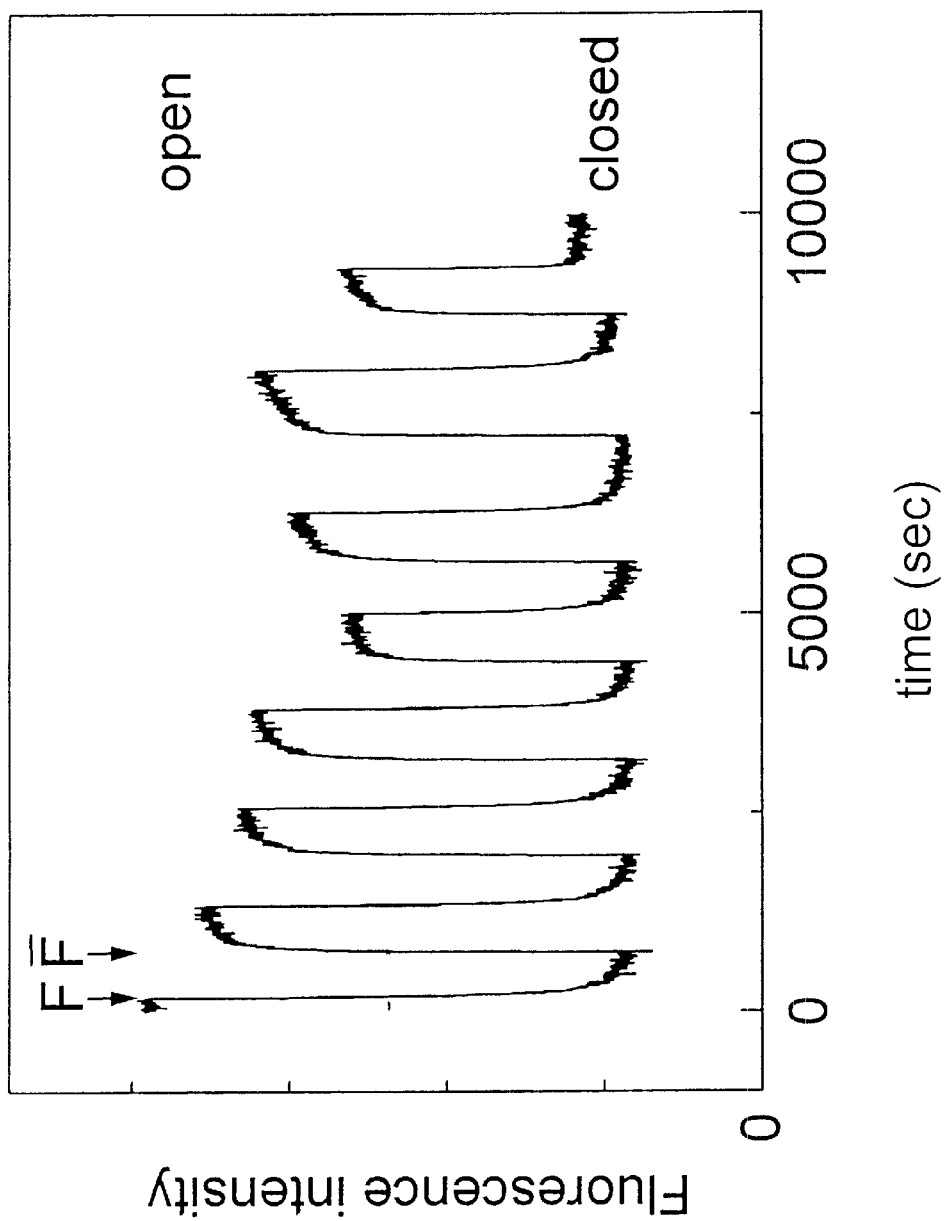
FIG. 6: Fluorometric data corresponding to cycling of the molecular tweezers. By adding stoichiometric quantities of fuel and removal strands F and $\overline{F}$ in sequence the tweezers may be closed and opened repeatedly. When the tweezers are closed, resonant energy transfer from the TET dye to the TAMRA moiety reduces the fluorescence intensity of the TET group.

Dye quenching is used to titrate the fuel and removal strands and to determine the state of the machine. The fluorescence intensity of the TET moiety drops by a factor of seven when the tweezers are closed, back to approximately the same level as from unhybridized, randomly-coiled A strands. FIG. 6 shows the variation in fluorescence intensity of the TET moiety as the tweezers are cycled eight times between the open and closed states by successive additions of strands F and $\overline{F}$. The switching time for the machine is approximately 20 s.

To calibrate the motion of the device we use modified fuel strands incorporating a central spacer section, inserted between the 24-base sequences of F that hybridize with the ends of strands B and C, to hold the ends of the tweezers at a fixed separation. The spacer consists of n bases (n=10, 15, 20, 40) hybridized to a complementary n-mer; its length is much less than the persistence length of double-stranded DNA so it acts as a rigid rod separating the tweezer ends. The fluorescence intensity from open tweezers (with free ends) is equal to the interpolated value for a 27-base spacer: we deduce an approximate value for the difference in the average separation between the ends of the tweezers in the open and closed states of 9 nm, corresponding to the open tweezer arms having an average angle of about 85°.

B. Assay for Stability of Closed Tweezer Structure

It is clear from FIG. 6 that the machine may be cycled repeatedly between two configurations in which the mean separation between the ends of the tweezers differs by about 9 nm. The recovery of a high fluorescence intensity in the open state indicates that the initial configuration, in which the two halves of A are straightened by hybridization with B and C, is recovered after each cycle. The low fluorescence intensity in the closed state tells us only that the dyes are relatively close together: it does not tell us whether the tweezer structure persists or whether, for example, strain at the hinge causes the arms of the tweezers to unravel. To test this we have used an additional strand $\overline{A}$, the complement of A, to dismantle the machine by displacing B and C from A. In the absence of other strands $\overline{A}$ hybridizes with A (producing a nine-fold increase in fluorescence intensity) with a half-life of 14 seconds. When a stoichiometric quantity of $\overline{A}$ is introduced to the same concentration of ready-formed tweezers in the open state the half-life for interaction is increased to 2.2×10$^4$ seconds by the need for thermally-activated displacement of parts of B and C from A before hybridization with $\overline{A}$ can begin. The interaction of $\overline{A}$ with tweezers held in the closed state is more than an order of magnitude slower than in the open state; the closed structure inhibits the winding and unwinding of strands that accompanies strand exchange. The high stability of the tweezers, even in the closed state where the hinge region is likely to be strained, indicates that its structural integrity is maintained.

C. Test for Non-productive Interactions Between Strands

We have also checked that when one of the tweezer components B, C is left out then changes in fluorescence intensity due to successive additions of F and $\overline{F}$ are less than 15% of the change achieved with the complete structure, and that there is no observable interaction between unhybridized strand A and either F or $\overline{F}$. We conclude that there are no significant unanticipated interactions between strands and that the machine operates as designed.

Conclusion

The present invention provides means for capturing the energy of nucleic-acid hybridization reactions and directing it to alter the configuration of a molecular machine in a controlled, and reversible or cyclic manner. It will be apparent to those skilled in the art that many possible embodiments, modifications, changes can be made without departing from the scope and spirit of the disclosed invention, and it is to be understood that all matter herein set forth or shown in the accompanying drawings and figures is to be interpreted as illustrative, and not in a limiting sense. It will be understood that certain features and subcombinations are of utility and may be employed without reference to other features and subcombinations. This is contemplated by and is within the scope of the claims. The scope of the invention should, therefore, be determined not with reference to the foregoing description, but should be determined with reference to the appended claims, along with the full scope of equivalents to which such claims are entitled.

REFERENCES

[1] L. E. Morrison and L. M. Stols, Biochemistry 32: 3095–3014 (1993).
[2] M. S. Ellwood et al., Clin. Chem. 32(9):1631–1636 (1986).
[3] C. P. H. Vary et al., Clin. Chem. 32(9):1696–1701 (1986).
[4] R. S. Quartin et al., Biochemistry 28: 8676–8682 (1989).
[5] D. M. Wong et al., Nucl. Acids Res. 19(9): 2251–2259 (1991).
[6] P. H. Weinstock et al., Nucl. Acids Res. 18(14): 4207–4213 (1989).
[7] Green et al., Nucl. Acids Res. 9(8): 1905–1918 (1981).
[8] Collins et al., Molecular and Cellular Probes 2: 15–30 (1988).
[9] G. M. Fahy, Clin. Chem. 39(9): 2011–2016 (1993).
[10] N. C. Seeman, Annu. Rev. Biophys. Biomed. Struct. 27: 225–248 (1998).
[11] E. Winfree, F. Lui, L. A. Wenzler, and N. C. Seeman, Nature 394: 539–544 (1998).
[12] C. Mao, W. Sun, and N. C. Seeman, Nature 386:138 (1997).
[13] Y. Zhang and N. C. Seeman, J. Am. Chem. Soc. 116: 1661–1669 (1994).
[14] J. Chen and N. C. Seeman, Nature 350: 631–633 (1991).
[15] J. Sambrook et al., 1989, *Molecular Cloning: A Laboratory Manual*, Second Edition, Books 1–3, Cold Spring Harbor Laboratory Press., 1989, *Molecular Cloning: A Laboratory Manual*, Second Edition, Books 1–3, Cold Spring Harbor Laboratory Press.
[16] B. Roe, J. Crabtree, and A. Kahn, 1996, *DNA Isolation and Sequencing: Essential Techniques*, John Wiley & Sons.
[17] J. M. Polak and James O'D. McGee, 1990, *In Situ Hybridization: Principles and Practice*, Oxford University Press.
[18] M. J. Gait (Editor), 1984, *Oligonucleotide Synthesis: A Practical Approach*, IRL Press.
[19] D. M. J. Lilley and J. E. Dahlberg, 1992, *Methods of Enzymology: DNA Structure Part A: Synthesis and Physical Analysis of DNA*, Methods in Enzymology, Vol. 211, Academic Press.
[20] J. D. Wilson, M. Gilman, J. Witkowski, and M. Zoller, 1992, *Recombinant DNA*, Second Edition, Scientific American Books.
[21] *Academic Press Dictionary of Science and Technology*, Edited by Christopher Morris, Academic Press Inc., San Diego, 1992. pp. 1289, 1417, 2149.
[22] *McGraw Hill Dictionary of Scientific and Technical Terms*, 3rd Edition, Edited by Sybil P. Parker, McGraw Hill Book Co., New York, 1984, pp. 951, 1046, 1593.
[23] S. Agrawal, 1993, *Protocols for Oligonucleotide Conjugates: Synthesis and Analytical Techniques* (Methods in Molecular Biology, Volume 26), edited by, Humana Press
[24] D. M. Gray, Biopolymers 42: 783 (1997).
[25] J. SantaLucia, Jr., H. T. Allawi, and P. A. Seneviratne, Biochemistry 35: 3555 (1996).
[26] K. J. Breslauer, R. Frank, H. Bloker, and L. A. Marky, Proc. Natl. Acad. Sci. USA 83: 3746 (1986).
[27] A. Ashkin, K. Schutze, J. M. Dziedzic, U. Euteneuer, and M. Schliwa, Nature 348: 346 (1990).
[28] S. C. Kuo and M. P. Sheetz, Science 260: 232 (1993).
[29] A. J. Hunt, F. Gittes, and J. Howard, Biophysical Journal 67: 766 (1994).
[30] K. Svoboda and S. M. Block, Cell 77: 773 (1994).
[31] A. Ishijima, Y. Harada, H. Kojima, T. Funatsu, H. Higuchi, and T. Yanagida, Biochemical and Biophysical Research Communications 199: 1057 (1994).
[32] J. T. Finer, R. M. Simmons, and J. A. Spudich, Nature 368: 113 (1994).
[33] J. E. Molloy, J. E. Burns, J. Kendrick-Jones, R. T. Tregear, and D. C. S. White, Nature 378: 209 (1995).
[34] G. McGall et al., U.S. Pat. No. 5,412,087.
[35] S. Fodor et al., U.S. Pat. No. 5,445,934.
[36] M. Heller et al., U.S. Pat. No. 5,605,662.
[37] C. Mirkin et al., Nature 382: 607–609, 1996.
[38] C. Cantor et al., U.S. Pat. No. 5,503,980.
[39] A. Marshall et al., Nature Biotechnology 16: 27–31, 1998.
[40] A. C. Pease et al., P.N.A.S. 91, pages 5022–26, 1994.
[41] A. K. Eggleston and S. C. Kowalczykowski, Biochemie 73: 163 (1991).
[42] M. J. Heller and L. E. Morrison, in *Rapid Detection and Identification of Infectious Agents*, edited by D. T. Kingsbury and S. Falkow, (Academic Press, New York 1985) pp. 245–256.
[43] X. Chen, B. Zehnbauer, A. Gnirke, and P-Y. Kwok, Proc. Natl. Acad. Sci. USA 94: 10756 (1997).
[44] In the preparation of all buffers ultrapure HPLC grade water (Alfa) was used. In preparation of SPSC buffers SigmaUltra monobasic sodium phosphate (Sigma), SigmaUltra dibasic phosphate (Sigma), and Puratonic 99.999% (metal basis) sodium chloride (Alfa) were employed. TRIZMA base and EDTA were purchased from Sigma.
[45] L. E. Morrison, T. C. Halder, and L. M. Stols, Anal. Biochem. 183: 231–244 (1989).
[46] R. J. Britten and D. E. Kohne, Science 161: 529 (1968).
[47] J. G. Wetmur and N. Davidson, J. Molecular Biology 31: 349 (1968).
[48] Alivisatos, A. P., Johnsson, K. P., Peng, X., Wilson, T. E., Loweth, C. J., Bruchez, M. P., Jr. & Schultz, P. G. Organization of 'nanocrystal molecules' using DNA. Nature 382, 609–611 (1996)
[49] Coffer, J. L., Bigham, S. R., Li, X., Pinizzotto, R. F., Rho, Y. G., Pirtle, R. M. & Pirtle, I. L. Dictation of the shape of mesoscale semiconductor nanoparticle assemblies by plasmid DNA Appl. Phys. Lett. 69, 3851–3853 (1996)
[50] Braun, E., Eichen, Y., Sivan, U. & Ben-Yoseph, G. DNA-templated assembly and electrode attachment of a conducting silver wire. Nature 391, 775–778 (1998)
[51] Mao, C., Sun, W., Shen, Z. & Seeman, N. C. A nanomechanical device based on the B-Z transition of DNA. Nature 397, 144–146 (1999)
[52] 50mM $Na_2HPO_4$ and 1M NaCl at pH 6.5
[53] Oligonucleotides were supplied by Integrated DNA Technologies, Inc; strand A was HPLC purified, other strands were PAGE purified.
[54] Smith, S. B., Finzi, L. & Bustamante, C. Direct Mechanical Measurements of the Elasticity of Single DNA Molecules by Using Magnetic Beads. Science 258, 1122–1126 (1992)
[55] Manning, G. S. A Procedure for Extracting Persistence Lengths from Light-Scattering Data on Intermediate Molecular Weight DNA. Biopolymers 20, 1751–175 5 (1981)

[56] Smith, S. B., Yujia, C. & Bustamante, C. Overstretching B-DNA: The Elastic Response of Individual Double-Stranded and Single-Stranded DNA Molecules. *Science* 271, 795–799 (1996)

[57] Tinland, B., Pluen, A., Sturm, J. & Weill, G. Persistence Length of Single-Stranded DNA. *Macromolecules* 30, 5763–5765 (1997)

[58] Stryer, L. & Haugland, R. P. Energy Transfer: A Spectroscopic Ruler. *Proc. Natl. Acad Sci. USA* 58, 719–726 (1967)

[59] SantaLucia, J., Jr., A unified view of polymer, dumbbell, and oligonucleotide DNA nearest-neighbor thermodynamics. *Proc. Nall. Acad Sci. USA*, 95, 1460–1465 (1998)

[60] Record, M. T., Jr., Anderson, C. F. & Lohman, T. M. Thermodynamic analysis of ion effects on the binding and conformational equilibria of proteins and nucleic acids: the roles of ion association or release, screening, and ion effects on water activity. *Quart. Rev. Biophys.* 11, 103–178 (1978)

[61] Bockelinann, U., Essevaz-Roulet, B. & Heslot, F. Molecular Stick-Slip Motion Revealed by Opening DNA with Piconewton Forces. *Phys. Rev. Lett.* 79, 4489–4492 (1997)

[62] Svoboda, K., Schmidt, C. F., Schnapp, B. J. & Block, S. M. Direct observation of kinesin stepping by optical trapping interferometry. *Nature* 365, 721–727 (1993)

[63] Green, C. & Tibbetts, C. Reassociation rate limited displacement of DNA strands by branch migration. *Nucleic Acids Research* 9, 1905–1918 (1981)

[64] Lee, C. S., Davis, R. W. & Davidson, N. A Physical Study by Electron Microscopy of the Terminally Repetitious, Circularly Permuted DNA from the Coliphage Particles of *Escherichia coli* 15. *J Mol. Biol.* 48, 1–22 (1970)

[65] Radding, C. M., Beattie, K. L., Holloman, W. K. & Wiegand, R. C. Uptake of Homologous Single-stranded Fragments by Superhelical DNA: IV Branch Migration. *J Mol. Biol.* 116, 825–839 (1977)

[66] Fu, T.-J. & Seeman, N. C. DNA double-crossover molecules. *Biochemistry* 32, 3211–3220 (1993)

[67] Turberfield, A. J., Yurke, B. & Mills, A. P., Jr. Coded Self-Assembly of DNA Nanostructures. *Bull. Am. Phys. Soc.* 44,1711 (1999).

[68] Tyagi, S., Bratu, D., & Kramer, F., Multicolor molecular beacons for allele discrimination. Nature Biotechnology, 16, 49–54 (1998).

We claim:

1. A nanomachine having alternative configurations, comprising:
   (a) a first molecular structure comprising a first oligomer strand the first oligomer strand coupled to a first portion of a molecular device;
   (b) a second molecular structure comprising a second oligomer strand the second oligomer strand coupled to a second portion of the molecular device;
   (c) a flexible linker moiety, one end of which is attached to the first molecular structure and the other end of which is attached to the second molecular structure; and
   (d) a third oligomer strand comprising:
      (i) a first subunit sequence that is hybridized to the first oligomer strand,
      (ii) a second subunit sequence that is hybridized to the second oligomer strand,
      (iii) a third, single-stranded subunit sequence that is not complementary to either the first or the second oligomer strand, and is configured to serve as a nucleation site for hybridization of the third oligomer strand to a fourth oligomer strand that is complementary to the third oligomer strand;
         wherein hybridization of the third oligomer strand to the first and second oligomer strands produces a force capable of moving the first and second portions of the molecular device closer to each other and;
      wherein hybridization of the fourth oligomer strand to the third oligomer strand is capable of causing dehybridization of the third oligomer strand from the nanomachine, resulting in a force capable of moving the first and second portions of the molecular device farther apart from each other.

2. The nanomachine of claim 1, wherein the first molecular structure her includes a first reactive group having a quenchable fluorescent moiety;
   the second molecular structure further includes a second reactive group having a fluorescence-quenching moiety; and
   the moving of the first and second portions of the molecular device closer to each other results in a detectable change in fluorescence.

3. The nanomachine of claim 1, wherein each of the first, second, third and fourth oligomer strands is independently a nucleic acid or a nucleic acid analog.

4. The nanomachine of claim 1, wherein the first, second, and third oligomer strands are DNA oligomers.

5. The nanomachine of claim 1, wherein the fourth oligomer strand is a DNA or an RNA oligomer.

6. The nanomachine of claim 1, wherein the first and second molecular structures are independently selected from the group consisting of a double-stranded nucleic acid, a double-stranded nucleic acid analog, a triple-stranded nucleic acid, a protein alpha helix, a protein triple helix and a synthetic, non molecular structure.

7. The nanomachine of claim 1, further comprising a molecular substrate to which one or both of the first and second oligomer strands are attached.

8. A nanomachine having alternative configurations, comprising:
(a) a first rod-like molecular structure which includes a first oligomer strand and a first reactive group, the first oligomer strand coupled to a first portion of the molecular device;
(b) a second rod-like molecular structure which includes a second oligomer strand and a second reactive group, the second oligomer strand coupled to a second portion of the molecular device;
wherein a change in a distance between the reactive groups occur upon hybridization of both the first and second oligomer strands to a third oligomer strand comprising;
(i) a first subunit sequence that is complementary to the first oligomer strand, and
(ii) a second subunit sequence that is complementary to the second oligomer strand, and
(iii) a third, single-stranded subunit sequence that is not complementary to the first or second oligomer strand, and is configured to serve as a nucleation site for hybridization of the third oligomer strand to a fourth oligomer strand that is complementary to the third oligomer strand;
wherein hybridization of the third oligomer to the first and second oligomer strands produces a force capable of moving the first and second portions of the molecular device closer to each other and the change in the distance between the reactive groups causes a detectable change in a signal produced by the reactive groups; and
wherein hybridization of the fourth oligomer strand to the third oligomer strand is capable of causing dehybridization of the third oligomer strand from the nanomachine, resulting in movement of the first and second portions of the molecular device farther apart from each other, and a second change in the distance between the reactive groups that causes a second detectable change in the signal produced by the reactive groups.

9. The nanomachine of claim 8, wherein the first reactive group is a quenchable fluorescent moiety;
the second reactive group is a fluorescence-quenching moiety; and
a change in the distance between the reactive groups results in a detectable change in fluorescence.

10. The nanomachine of claim 8, wherein each of the first, second, third and fourth oligomer strands is independently a nucleic acid or a nucleic acid analog.

11. The nanomachine of claim 8, wherein the first, second, and fourth oligomer strands are DNA oligomers.

12. The nanomachine of claim 8, wherein the third oligomer strand is a DNA or an RNA oligomer.

13. The nanomachine of claim 8, wherein the first and second rod-like molecular structures are independently selected from the group consisting of a double-stranded nucleic acid, a double-stranded nucleic acid analog, a triple-stranded nucleic acid, a protein alpha helix, a protein triple helix, and a synthetic, non-natural molecular structure.

14. The nanomachine of claim 8, further comprising a molecular substrate to which one or both of the first and second oligomer strands are attached.

15. A method for moving portions of a molecular device, comprising mixing in a solution,
(1) a nanomachine comprising:
(a) a first molecular structure comprising a first oligomer strand the first oligomer strand coupled to a first portion of a molecular device;
(b) a second molecular structure comprising a second oligomer strand the second oligomer strand coupled to a second portion of the molecular device;
(c) a flexible linker moiety, one end of which is attached to the first molecular structure and the other end of which is attached to the second molecular structure; and
(d) a third oligomer strand comprising
(i) a first subunit sequence that is hybridized to the first oligomer strand,
(ii) a second subunit sequence that is hybridized to the second oligomer strand,
(iii) a third, single-strand subunit sequence that is not complementary to either the first or second oligomer strand, and is configured to serve as a nucleation site for hybridization of the third oligomer strand to a fourth oligomer strand that is complementary to the third oligomer strand;
wherein the hybridization of the third oligomer to the first and second oligomers produces a force capable of moving the first and second portions of the molecular device closer to each other; and then mixing in the solution
(2) a fourth oligomer strand that is complementary to the third oligomer strand, under conditions in which the fourth oligomer strand hybridizes specifically to the third oligomer strand, causing dehybridization of the third oligomer strand from the nanomachine resulting in a force capable of moving the first and second portions of the molecular device farther apart from each other.

16. The method of claim 15, wherein the first molecular structure further includes a first reactive group having is a quenchable fluorescent moiety;
the second molecular structure further includes a second reactive group having is a fluorescence-quenching moiety; and
the moving of the first and second portions of the molecular device closer to each other results in a detectable change in fluorescence.

17. The method of claim 15, wherein the fourth oligomer strand is a DNA or an RNA oligomer.

18. The method of claim 15, wherein one or both of the first and second oligomer strands are attached to a molecular substrate.

19. A method for moving portions of a molecular device and producing a detectable signal comprising mixing in a solution,
(1) a nanomachine comprising:
(a) a first rod-like molecular structure which includes a first oligomer strand and a first reactive group, the first oligomer strand coupled to a first portion of a molecular device; and
(b) a second rod-like molecular structure which includes a second oligomer strand and a second reactive group, the second oligomer strand coupled to a second portion of the molecular device;
(2) a third oligomer strand comprising:
(a) a first subunit sequence that is complementary to the first oligomer strand, (b) a second subunit sequence that is complementary to the second oligomer strand, and (c) a third, single-stranded subunit sequence that is not complementary to either the first or second oligomer strand, and is configured to serve as a nucleation site for hybridization of the third oligomer strand to a fourth oligomer strand that is complementary to the third oligomer strand;

under conditions in which the first and second oligomer strands hybridizes specifically to the first and second subunit sequences, respectively, of the third oligomer strand thereby producing a force capable of moving the first and second portions of the molecular device closer to each other and changing a distance between the reactive groups thereby causing a detectable change in a signal produced by the reactive groups; and then (3) mixing in the solution a fourth oligomer strand wherein hybridization of the fourth oligomer strand to the third oligomer strand causes dehybridization of the third oligomer strand from the nanomachine, resulting in movement of the first and second portions of the molecular device farther apart from each other, and a second change in the distance between the reactive groups that causes a second detectable change in the signal produced by the reactive groups.

20. The method of claim 19, wherein the first reactive group is a quenchable fluorescent moiety, the second reactive group is a fluorescence-quenching moiety; and a change in the distance between the reactive groups results in a detectable change in fluorescence.

21. The method of claim 19, wherein the fourth oligomer strand is an DNA or an RNA oligomer.

22. The method of claim 19, wherein one or both of the first and second oligomer strands are attached to a molecular substrate.

23. The method of claim 19, further comprising mixing in a solution, (1) the complex formed by hybridization of the third oligomer strand to the first and second oligomer strands of a nanomachine, and (2) a fourth oligomer strand that is complementary to the third oligomer strand, under conditions in which the fourth oligomer strand hybridized specifically to the third oligomer strand, thereby removing the third oligomer strand from the nanomachine.

* * * * *

UNITED STATES PATENT AND TRADEMARK OFFICE
CERTIFICATE OF CORRECTION

PATENT NO. : 6,696,285 B1
DATED : February 24, 2004
INVENTOR(S) : Allen P. Mills, Jr. and Bernard Yurke It is certified that error appears in the above-identified patent and that said Letters Patent is hereby corrected as shown below:

Title page,
Add Item -- [73] Assignee: Lucent Technologies Inc., Murray Hill, N.J. --

Signed and Sealed this

Fifth Day of October, 2004

JON W. DUDAS
*Director of the United States Patent and Trademark Office*